US009045725B2

(12) United States Patent
Vogel et al.

(10) Patent No.: US 9,045,725 B2
(45) Date of Patent: Jun. 2, 2015

(54) DEVICES AND METHODS FOR INTEGRATED CONTINUOUS MANUFACTURING OF BIOLOGICAL MOLECULES

(75) Inventors: Jens Holger Vogel, Richmond, CA (US); Roberto Giovannini, Neuchatel (CH); Konstantin B. Konstantinov, Waban, MA (US); Huong My Nguyen, San Francisco, CA (US); Paul Wu, Orinda, CA (US)

(73) Assignee: Bayer Healthcare LLC, Whippany, NJ (US)

( * ) Notice: Subject to any disclaimer, the term of this patent is extended or adjusted under 35 U.S.C. 154(b) by 913 days.

(21) Appl. No.: 11/576,097

(22) PCT Filed: Sep. 30, 2005

(86) PCT No.: PCT/US2005/035364
§ 371 (c)(1),
(2), (4) Date: Apr. 3, 2008

(87) PCT Pub. No.: WO2006/039588
PCT Pub. Date: Apr. 13, 2006

(65) Prior Publication Data
US 2008/0269468 A1    Oct. 30, 2008

Related U.S. Application Data

(60) Provisional application No. 60/614,995, filed on Sep. 30, 2004.

(51) Int. Cl.
| C07K 1/34 | (2006.01) |
| C07K 1/18 | (2006.01) |
| C12N 5/02 | (2006.01) |
| C12N 5/07 | (2010.01) |
| C12M 1/00 | (2006.01) |
| C07K 1/14 | (2006.01) |
| B01D 61/14 | (2006.01) |
| C07K 14/755 | (2006.01) |
| A61K 38/00 | (2006.01) |

(52) U.S. Cl.
CPC ............ *C12M 47/12* (2013.01); *C07K 1/14* (2013.01); *B01D 61/145* (2013.01); *B01D 2311/14* (2013.01); *B01D 2311/16* (2013.01); *B01D 2313/10* (2013.01); *B01D 2313/18* (2013.01); *B01D 2317/04* (2013.01); *C07K 1/145* (2013.01); *C07K 1/34* (2013.01); *C07K 14/755* (2013.01)

(58) Field of Classification Search
CPC ........................................................ C07K 1/34
See application file for complete search history.

(56) References Cited

U.S. PATENT DOCUMENTS

| 5,157,113 | A | * | 10/1992 | Dove et al. ................. 530/388.1 |
| 5,256,294 | A | | 10/1993 | van Reis |
| 5,490,937 | A | * | 2/1996 | van Reis ........................ 210/637 |
| 5,616,595 | A | | 4/1997 | Chu et al. ........................ 514/344 |
| 6,232,448 | B1 | * | 5/2001 | Yoshikubo et al. ....... 530/388.26 |
| 6,350,382 | B1 | | 2/2002 | Schick ........................... 210/637 |
| 6,544,242 | B1 | | 4/2003 | Kido et al. |
| 2003/0096011 | A1 | * | 5/2003 | Tracy et al. ................... 424/486 |
| 2004/0022805 | A1 | * | 2/2004 | Narum et al. .............. 424/191.1 |
| 2004/0139864 | A1 | * | 7/2004 | Kopf et al. ........................ 99/495 |
| 2004/0167320 | A1 | | 8/2004 | Couto et al. |
| 2005/0009022 | A1 | * | 1/2005 | Weiner et al. ..................... 435/6 |
| 2005/0197496 | A1 | | 9/2005 | Perreault |
| 2006/0172376 | A1 | * | 8/2006 | Chadjaa et al. .............. 435/69.1 |

FOREIGN PATENT DOCUMENTS

| JP | 06-500730 | 4/1992 |
| JP | 08-503614 | 6/1994 |
| JP | 10-500847 | 11/1995 |
| WO | WO 03/003979 | 1/2003 |
| WO | WO 2004/076695 | 9/2004 |

OTHER PUBLICATIONS

Amersham Biosci (2001) Application note, 18/1150-21, Cost comparison: expanded bed adsorption (EBA) vs conventional recovery in the industrial scale processing of proteins, pp. 15.*
Mochizuki et al. (1992) Effect of Protein Adsorption on the Transport Characteristics of Asymmetric Ultrafiltration Membranes, vol. 8, pp. 553-561.*
Kaufmann M. (1997) Unstable proteins: how to subject them to chromatographic separations for purification procedures, J. Chromatogr. (B) Biomed. Sci. Appl. vol. 699, issue 1-2, pp. 347-369.*
Vogel, et al., "Integration of isolation and continuous perfusion fermentation of recombinant biopharmaceuticals", American Chemical Society, Mar. 1, 2004, vol. 227, Abstract only.
International Search Report from International Application No. PCT/US05/035364, International Publication No. 2006/039588, mailed on Feb. 21, 2007.

(Continued)

*Primary Examiner* — Jon P Weber
*Assistant Examiner* — Samuel Liu
(74) *Attorney, Agent, or Firm* — McDonnell Boehnen Hulbert & Berghoff LLP

(57) ABSTRACT

The present invention relates to a process and apparatus for purifying a molecule of interest from a heterogeneous clarified fluid mixture. The apparatus of the invention generally comprises a continuous perfusion fermentation system, a continuous particle removal system integrated with the perfusion fermentation system; and a continuous purification system integrated with the particle removal system, which is maintained under sterile conditions. The process comprises filtering a heterogeneous clarified fluid mixture by continuous ultrafiltration at a specific flow rate below the transition point of the molecule of interest in the pressure-dependent region of the flux versus TMP curve, wherein the specific flow rate is maintained substantially constant throughout the continuous ultrafiltration.

4 Claims, 17 Drawing Sheets

(56) References Cited

OTHER PUBLICATIONS

Supplementary European Seach Report from European Application No. EP 05800224.7, completed Feb. 15, 2010.

Vogel, Jens H., et al., "Continuous isolation of rFVIII from Mammalian Cell Culture", *Animal Cell Technology: From Target to market*, 2011, pp. 313-317.

Voisard, D, et al., "Potential of Cell Retention Techniques for Large-Scale High-Density Perfusion Culture of Suspended Mammalian Cells", *Biotechnology and Bioengineering*, Jun. 30, 2003, vol. 82(7), pp. 751-765, doi: 10.1002/bit.10629.

Woodside, Steven M., "Mammalian Cell Retention Devices for Stirred Perfusion Bioreactors", *Cytotechnology*, 1998, vol. 28, pp. 163-175.

Yavorsky, David, et al., "The Clarification of Bioreactor of Cell Cultures for Biopharmaceuticals", *Pharmaceutical Technology*, Mar. 2003, pp. 2-9.

* cited by examiner

DEVICES AND METHODS FOR INTEGRATED CONTINUOUS MANUFACTURING OF BIOLOGICAL MOLECULES

FIELD OF THE INVENTION

The present invention relates to an improved method and system for purifying a molecule of interest from a heterogeneous mixture of molecules. More particularly, the present invention is directed to methods for purifying a protein of interest in a tissue culture fluid feedstream from a continuous perfusion fermentation process.

BACKGROUND OF THE INVENTION

It is well known to those familiar with the field that in recent years several continuous cell culture processes, also called continuous perfusion processes, have been established with great commercial success. However, the isolation process following continuous perfusion fermentation is generally a batch process, and is physically and logistically separated from the continuous upstream process. In these processes, the main purpose of the isolation step is to capture the product out of high volumes of relatively dilute culture supernatant. Concentration of the product has to be emphasized with respect to process logistics and space requirements, while simultaneous removal of contaminants (purification) is important to minimize the required number of further downstream purification steps.

FIG. 1 shows a schematic of a typical state-of-the-art isolation process from continuous perfusion fermentation, as it is well known to those familiar with the field. The continuous perfusion fermentation system comprises a cell retention device (1), which keeps most of the cells producing the product in the fermentation system. A continuous harvest stream from the continuous perfusion system, still containing some cells, debris and other particles is pumped using a harvest pump (2) into large collection vessels (3), such as stainless steel tanks. These harvest storage vessels usually have to be cooled in order to keep product losses due to degradation within a feasible range.

Once a specified volume has been collected, which is typically after 1-4 days or more, the harvest collection vessels are disconnected from the sterile fermentation vessel and the collected material is designated as one harvest batch. The next step is to remove cells, debris and particles (step 2). In industrial scale this is typically done using centrifugation (4) followed by dead-end membrane filtration (5), or by dead-end depth-filtration (6) followed by dead-end membrane filtration (7). Another technique sometimes used is tangential flow (or "crossflow") microfiltration. In any case, the product of the particle removal process is a batch of clarified tissue culture fluid, or cTCF (8). More details on particle separation for biotechnological products can be found in standard textbooks, such as Biotechnology, Vol. 3, Bioprocessing, Wiley-VCH, 2 edition (1996), ISBN: 3527283137.

In the next step (step 3), the batch of clarified tissue culture fluid is further processed to concentrate and, if possible, purify the product. This is typically done by crossflow ultrafiltration or by packed bed chromatography.

In the case of crossflow ultrafiltration, the cTCF is pumped into the recycle tank (9) of the system. A pump is used (10) to push the material through a crossflow ultrafilter. The product is retained by the membrane and recycled as retentate into the recycle tank, while water and smaller contaminants are pushed through the membrane into the permeate (11) due to the trans-membrane pressure generated by the pressure drop in the ultrafiltration module. In each passage through the filter, the cTCF therefore gets more concentrated, and the total cTCF volume is reduced until a desired concentration factor is reached. Once the desired concentration factor is reached, the process is stopped, and the remaining concentrate volume (isolate) is drained from the system and collected. More details on crossflow ultrafiltration for concentration of biotechnological products can be found in standard textbooks, such as Biotechnology, Vol. 3, Bioprocessing, Wiley-VCH, 2 edition (1996), ISBN: 3527283137.

In case of packed bed chromatography, the cTCF is pumped over a chromatography column (12) containing a packed resin bed. The product binds to the resin and is then eluted in usually concentrated and purified form (isolate, 13) using a suitable elution buffer (14), after which the column is cleaned and regenerated using adequate buffers and cleaning solutions (14).

Other chromatography variants that have been proposed for concentration/purification of cTCF are expanded bed chromatography and membrane chromatography. Expanded bed chromatography can process particle containing solutions. However, filtration of the isolate after chromatography is still required, although filtration areas are reduced. Membrane chromatography utilizes stacks of modified microfiltration membranes instead of packed resin beds. The advantage is that mass transfer is largely convective rather then diffusive, which allows faster separation. Otherwise, the process is typically equivalent to standard packed bed chromatography. More details on chromatography for concentration and purification of biotechnological products can be found in standard textbooks, such as Protein Purification, Principles, High-Resolution Methods, and Applications, Wiley-VCH, 2. Edition (1998), ISBN 0-471-18626-0.

Often, the bulk isolate is then frozen and stored for later use in further downstream purification steps.

Thus, as described above, the isolation process is generally a batch process, and is physically and logistically separated from the continuous upstream process. Also, while fermentation has to be performed sterile, isolation (i.e. particle removal and concentration/purification) is essentially performed clean, but not sterile.

The state-of-the-art processes as described above have a number of problems:

P1. Yield losses and potential quality reduction due to high product residence time. The harvest from the continuous perfusion fermentation needs to be collected and stored over significant periods of time, as outlined above, before an isolation batch can be processed. Collected harvest, although chilled, still provides a detrimental milieu for complex and inherently unstable protein products. Therefore, significant product losses occur, which reduces plant capacity and increases cost of goods. Furthermore, the product quality can be adversely affected.

P2. Large cold room facilities or cooled vessels are required for intermediate storage of large harvest volumes, leading to high capital costs and negating the cited compactness and mobility advantage of perfusion fermenters.

P3. Conventional concentration/purification technologies (e.g., ultrafiltration, packed bed chromatography) have relatively low volumetric throughput, significant turnaround times and are relatively labor intensive. As a result, typically not more then 1 batch process is performed per day.

P4. Moreover, current isolation processes and methods have logistical difficulties dealing with the varying process volumes in fermentation plants involving more then one fermenter. In large-scale continuous perfusion plants, a varying number of fermenters are operational.

P5. Furthermore, state-of-the-art isolation processes are operated clean, but can not be operated sterile. This often leads to a significant number of rejected batches due to microbial load issues.

P6. Utilization of disposables, such as disposable filters, assemblies, bags, etc., although very desirable in the production of human parenterals (e.g., to avoid cleaning and cleaning validation and other issues) is very costly, and in fact often not economical.

Accordingly, it is an object of the present invention to provide a integrated, continuous protein separation process that is capable of operating for sustained periods of time under sterile conditions.

SUMMARY OF INVENTION

The present invention is directed to a novel apparatus and process for purifying molecules from a heterogeneous fluid mixture. More particularly, the invention is directed to a process for purifying a molecule of interest from a heterogeneous clarified fluid mixture from which particulate contaminants have been removed. The process comprises the step of filtering a heterogeneous clarified fluid mixture by continuous ultrafiltration at a specific flow rate below the transition point of the molecule of interest in the pressure-dependent region of the flux versus transmembrane pressure (TMP) curve, wherein the specific flow rate is maintained substantially constant throughout the continuous ultrafiltration.

In particular embodiments, the process of the invention comprises filtering the clarified fluid mixture through an ultrafiltration membrane having an area in square meters approximately equal to between 0.1 to 2 times the volumetric flow rate of the clarified fluid mixture in liters/hour. In another embodiment, the process of the invention comprises filtering the clarified fluid mixture through an ultrafiltration membrane having an area in square meters approximately equal to between 0.3 to 1 times the volumetric flow rate of the clarified fluid mixture in liters/hour.

The process of the invention advantageously permits filtering the clarified mixture at a specific flow rate that produces a wall concentration less than about 20%, less than 15% or less than 10% greater than the retentate concentration, without appreciable concentration polarization.

In a more specific embodiment, the invention is directed to an integrated, continuous and sterile process for continuous perfusion fermentation, particulate removal and purification/concentration. In one aspect of the invention, the process comprises filtering the tissue culture mixture by a separation process that selectively separates the protein of interest from the mixture at an operational set point below the transition point of the protein in the pressure-dependent region of the flux versus TMP curve to produce a sterile, particle-free, concentrated and partially purified product isolate, where the specific flow rate through the separation process is maintained substantially constant at a level less than the transition point of the protein.

In another aspect of the invention, the process is a continuous process for purifying a protein of interest from a heterogeneous tissue culture fluid mixture, comprising:

(a) producing by a continuous perfusion fermentation process a heterogeneous tissue culture fluid mixture containing a protein of interest;

(b) transferring the tissue culture fluid mixture to a continuous particle removal process integrated with the continuous perfusion fermentation process;

(c) removing particulate contaminants from the tissue culture fluid in the continuous particle removal process to produce a clarified tissue culture fluid containing the protein of interest;

(d) transferring the clarified tissue culture fluid to a continuous purification process integrated with the continuous particle removal process; and (e) purifying the protein of interest from the clarified tissue culture fluid in the continuous purification process;

wherein the specific flow rate of the mixture through the continuous perfusion fermentation process, continuous particle removal process and continuous purification process is maintained substantially constant.

In yet another aspect of the invention, the process is a semi-continuous process for purifying a protein of interest from a heterogeneous tissue culture fluid mixture, comprising:

(a) producing by a continuous perfusion fermentation process a heterogeneous tissue culture fluid mixture containing a protein of interest;

(b) transferring the tissue culture fluid mixture to a continuous particle removal process integrated with the continuous perfusion fermentation system;

(c) removing particulate contaminants from the tissue culture fluid in the continuous particle removal process to produce a clarified tissue culture fluid containing the protein of interest;

(d) transferring the clarified tissue culture fluid to a surge vessel integrated with the continuous particle removal process;

(e) intermittently transferring the clarified tissue culture fluid to a purification process integrated with the surge vessel; and (e) purifying the protein of interest from the clarified tissue culture fluid in the purification system to produce a sterile, particle-free, concentrated and partially purified product isolate containing the protein of interest;

wherein the specific flow rate of the mixture through the continuous perfusion fermentation process and continuous particle removal process is maintained substantially constant.

The present invention is also directed to an apparatus for separating a protein of interest from a heterogeneous tissue culture fluid mixture. In one aspect of the invention, the apparatus comprises: (a) a continuous perfusion fermentation system; (b) a continuous particle removal system integrated with the perfusion fermentation system; and (c) a continuous purification system integrated with the particle removal system, wherein the apparatus is adapted to maintain sterile conditions.

In another aspect of the invention, the apparatus comprises: (a) a continuous perfusion fermentation system; (b) a continuous particle removal system integrated with the perfusion fermentation system; and (c) an intermittent purification system integrated with the particle removal system, wherein the apparatus is adapted to maintain sterile conditions.

The purification system may, for example, be an ultrafiltration system or a convective adsorption/desorption system, or any other system capable of purifying or partially purifying a protein of interest from a heterogeneous mixture in an integrated, continuous or semi-continuous, sterile system as described herein.

The process and apparatus of the invention are adapted to permit continuous processing of a heterogeneous fluid mixture, such as a cell culture fluid, at a substantially constant flow rate. In a particular aspect of the invention, the process and apparatus of the invention are adapted to permit continuous processing of a heterogeneous cell or tissue culture fluid mixture at a substantially constant flow rate below the transition point of the protein in the pressure-dependent region of the flux versus TMP curve for a continuous period and throughout the purification process.

These and other aspects of the invention are described in detail below in the following detailed description of the invention.

BRIEF DESCRIPTION OF THE DRAWINGS

The accompanying drawings, which are incorporated in and constitute a part of the specification, illustrate embodiments of the invention, and, together with the detailed description of the embodiment, serve to explain the principles of the invention and its benefits.

DETAILED DESCRIPTION OF THE INVENTION

Definitions

Figure 1:
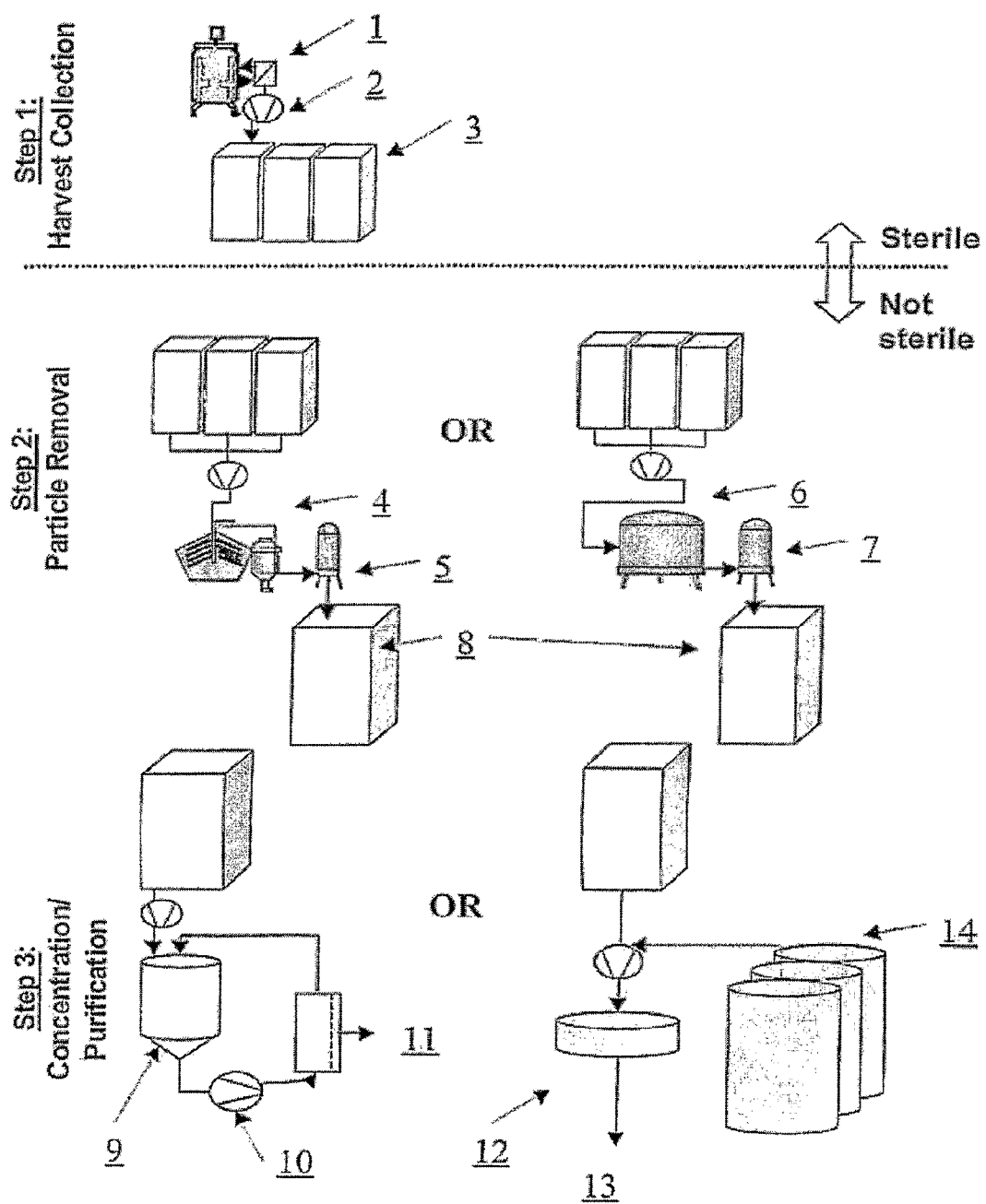
FIG. 1: Schematic of conventional continuous perfusion process followed by 3 physically and logistically segregated isolation process steps (batch harvest collection, batch particle removal and batch concentration/purification)

Except as expressly defined herein, the terminology used in this application is standard within the art. The following definitions of certain terms are provided herein to assure clarity and definiteness to the meaning of the claims.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "clarification" and "clarified" mean the removal of particulate matter from a solution so that the remaining solution passes through a 0.2 µm membrane.

The term "continuous perfusion fermentation" refers to a steady state fermentation system or process that operates without interruption and in which cells or micro-organisms are maintained in culture in the exponential growth phase by the continuous addition of fresh medium that is balanced by the removal of cell suspension from the bioreactor.

The terms "cultivating," "culturing," "growing," "maintaining," "supporting," and "expanding" are synonymous in meaning that cells remain viable and capable of producing progeny.

The term "concentration," in its verb form, means the removal of water from a solution such that the amount of a molecule of interest per volume of remaining solution increases.

The term "concentration polarization" means the accumulation of retained molecules (gel layer) on the surface of the membrane caused by a combination of factors: transmembrane pressure, crossflow velocity, sample viscosity, and solute concentration.

The term "continuous," means uninterrupted in time, sequence and/or operation for prolonged periods of time. As used in reference to the fermentation, clarification and filtration processes of the present invention, "continuous" means that the processes are physically and logistically integrated so as to permit operation without interruption for a prolonged period of time sufficient to produce a sterile, particle-free, concentrated and partially purified product isolate containing the protein of interest. The term continuous, as used in reference to the processes of the invention, is also understood to mean that a process is not performed in a batch-wise manner or in a truly continuous manner. The processes of the present invention are capable of continuous operation, for example, for prolonged periods ranging from 1 day to several months without interrupting the operation or sequence of the processes. As used in the present invention, the processes are operated for a continuous period greater than 2, 3, 4, 5, 6, or 7 days, 2, 3, 4, 5, 6, 7 or 8 weeks, or 3, 4, 5, 6 or more months.

The terms "semi-continuous" and "intermittent" mean that one or more processes or elements of an integrated system operate in a discontinuous or batch-wise manner, while other processes or elements of the integrated system operate in a continuous manner. For example, in some embodiments of the invention, the purification process is a convective adsorption/desorption process, which typically requires adsorption of the heterogeneous mixture of an adsorption substrate, eventually resulting in saturation of the substrate, and which requires termination of the adsorption process and desorption or release of the bound fraction. Such a process is inherently intermittent, though capable of being integrated with upstream processes that are continuous.

The term "convective adsorption/desorption" means a chromatographic process in which mass transfer occurs primarily by convection. Convective adsorption/desorption is a process in which a fraction of a mixture containing a molecule of interest is separated from another fraction of the mixture, by means of adsorption of one fraction to a substrate followed by desorption of that fraction from the substrate.

The term "crossflow" or "fluid crossflow" means the flow of the fluid across the top of the membrane surface.

The term "integrated," as used in reference to multiple systems and/or processes, means that the systems and/or processes are physically and logistically connected so as to constitute a unified system capable of operating continuously. In the context of the system of the present invention, which is directed to an integrated continuous or semi-continuous system for producing a particle-free, concentrated and partially purified protein of interest, an integrated system will connect different components directly and in a manner sufficient to maintain sterile conditions between the different components of the system.

The terms "media" (plural) and "medium" (singular) are synonymous and are used interchangeably herein, and use of one form of the term does not imply exclusion of the other form.

The term "mixture" means a heterogeneous combination of molecules and compounds containing a molecule of interest, such as a protein, and various contaminants. A preferred mixture of the current invention is a tissue culture fluid comprised of a heterogeneous mixture of proteins including an exogenous protein of interest, which is obtained initially from a continuous perfusion fermentation process.

The term "gel layer" means the microscopically thin layer of molecules that can form on the top of a membrane. It can affect retention of molecules by clogging the membrane surface and thereby reduce the filtrate flow, or, in constant flow operation, increase TMP.

The term "molecule of interest" means particles or other species of molecule that is to be separated from a solution or suspension in a fluid (e.g., a liquid). The particles or molecules of interest are separated from the fluid and, in most instances, from other particles or molecules in the fluid. The size of the molecule of interest to be separated will determine the pore size of the membrane to be utilized. Preferably, the molecules of interest are of biological or biochemical origin or produced by transgenic or in vitro processes and include proteins, peptides, polypeptides, antibodies or antibody fragments. Examples of preferred feedstream origins include mammalian cell culture and microorganism cell culture such as bacteria, fungi, and yeast. It should also be noted that species to be filtered out include non-desirable polypeptides, proteins, cellular components, DNA, colloids, mycoplasm, endotoxins, viruses, carbohydrates, and other molecules of biological interest, whether glycosylated or not.

The term "permeate" is used synonymously with filtrate.

The term "product isolate" means a particle-free, concentrated and partially purified product containing a protein of interest. A product isolate is a product that has achieved a degree of purification and concentration comparable to that achieved by an ultrafiltration or convective adsorption/desorption process. A product isolate is not necessarily homogeneous, but will be substantially purified relative to the initial bulk product produced by the fermentation process.

The term "specific flow rate" is used interchangeably with the term "filtrate flux" as it relates to the filtrate. The specific retentate flow rate is the flow rate of the retentate normalized on the membrane area used.

As used in reference to flux, the term "substantially constant" means that the flux is maintained at a generally constant level during a substantial period during the course of the filtration.

The term "tissue culture fluid" means a heterogeneous mixture of components derived from a tissue culture medium. In preferred aspects of the invention, the tissue culture fluid is derived from a continuous perfusion fermentation process. A "clarified" tissue culture fluid is a tissue culture fluid that has been prefiltered to remove cell debris and other large macromolecules.

The term "transmembrane pressure" and its acronym "TMP" mean the average applied pressure from the feed to the filtrate side of the membrane. TMP is calculated by TMP [bar]=[(PF+PR)/2]−Pf where PF is the feed pressure, PR is the retentate pressure, and Pf is the filtrate pressure.

The term "recovery" means the amount of a molecule of interest that can be retrieved after processing. Usually expressed as a percentage of starting material or yield.

The term "retentate" means the portion of the sample that does not pass through the membrane, also known as the concentrate.

The term "ultrafiltration" means a form of filtration that uses microporous or semipermeable membranes to preferentially separate fluids or ions on the basis of differential size or molecular weight. Ultrafiltration is typically used to filter out molecules having a molecular weight larger than about 10,000 daltons.

The present invention is directed to an integrated, continuous and sterile process comprising continuous perfusion fermentation, particulate removal and purification/concentration. In one aspect of the invention, the process comprises filtering the tissue culture mixture by a separation process that selectively separates the protein of interest from the mixture at an operational set point below the transition point of the protein in the pressure-dependent region of the flux versus TMP curve to produce a sterile, particle-free, concentrated and partially purified product isolate, where the specific flow rate through the separation process is maintained substantially constant at a level less than the transition point of the protein.

In another aspect of the invention, the process is a continuous process comprising: (a) continuously producing by continuous perfusion fermentation a heterogeneous tissue culture fluid mixture containing a protein of interest; (b) continuously transferring the tissue culture fluid mixture to a particle removal process integrated with the continuous perfusion fermentation system; (c) continuously removing particulate contaminants from the tissue culture fluid in the particle removal process to continuously produce a clarified tissue culture fluid containing the protein of interest; (d) continuously transferring the clarified tissue culture fluid to a purification process integrated with the particle removal system; and (e) continuously separating the protein of interest from the clarified tissue culture fluid in the purification system to continuously produce a sterile, particle-free, concentrated and partially purified product isolate containing the protein of interest.

In yet another aspect of the invention, the process is a semi-continuous process comprising: (a) continuously producing by continuous perfusion fermentation a heterogeneous tissue culture fluid mixture containing a protein of interest; (b) continuously transferring the tissue culture fluid mixture to a particle removal process integrated with the continuous perfusion fermentation system; (c) continuously removing particulate contaminants from the tissue culture fluid in the particle removal process to continuously produce a clarified tissue culture fluid containing the protein of interest; (d) continuously transferring the clarified tissue culture fluid to a surge vessel integrated with the particle removal process; (e) intermittently transferring the clarified tissue culture fluid to a purification process integrated with the surge vessel; and (e) separating the protein of interest from the clarified tissue culture fluid in the purification system to produce a sterile, particle-free, concentrated and partially purified product isolate containing the protein of interest, wherein the specific flow rate of the mixture through the continuous perfusion fermentation process and continuous particle removal process is maintained substantially constant, and on average equals the time-averaged throughput of the integrated semi-continuous purification process.

Devices for Practicing Methods of Invention

The present invention is also directed to an apparatus for separating a protein of interest from a heterogeneous tissue culture fluid mixture. Generally, the apparatus comprises: (a) a continuous perfusion fermentation system; (b) a continuous particle removal system integrated with the perfusion fermentation system; and (c) a continuous purification system integrated with the particle removal system, wherein the apparatus is adapted to maintain sterile conditions. In another aspect of the invention, the apparatus comprises: (a) a continuous perfusion fermentation system; (b) a continuous particle removal system integrated with the perfusion fermentation system; and (c) an intermittent purification system integrated with the particle removal system, wherein the apparatus is adapted to maintain sterile conditions. The purification system may, for example, be an ultrafiltration system or a convective adsorption/desorption system, or any other system capable of purifying or partially purifying a protein of interest from a heterogeneous mixture in an integrated, continuous or semi-continuous, sterile system as described herein.

The process and apparatus of the invention are adapted to permit continuous processing of a heterogeneous tissue culture fluid mixture at a substantially constant flow rate. In a particular aspect of the invention, the process and apparatus of the invention are adapted to permit continuous processing of a heterogeneous tissue culture fluid mixture at a substantially constant flow rate below the transition point of the protein in the pressure-dependent region of the flux versus TMP curve for a continuous period and throughout the purification process.

In specific embodiments, the invention provides two novel devices (A, B) which are each composed of 3 distinct but fully integrated elements, all of which have an essential role and together form a uniquely efficient, continuous protein isolation system platform that solves the problems with the prior art described above.

The three distinct elements of each device are firstly an integrated, continuous particle removal system (100), secondly a sterile surge vessel (200) and thirdly an integrated concentration/purification system (300,400, respectively). All three elements and thereby the developed novel devices and methods of using these devices are described in detail below.

Figure 2:
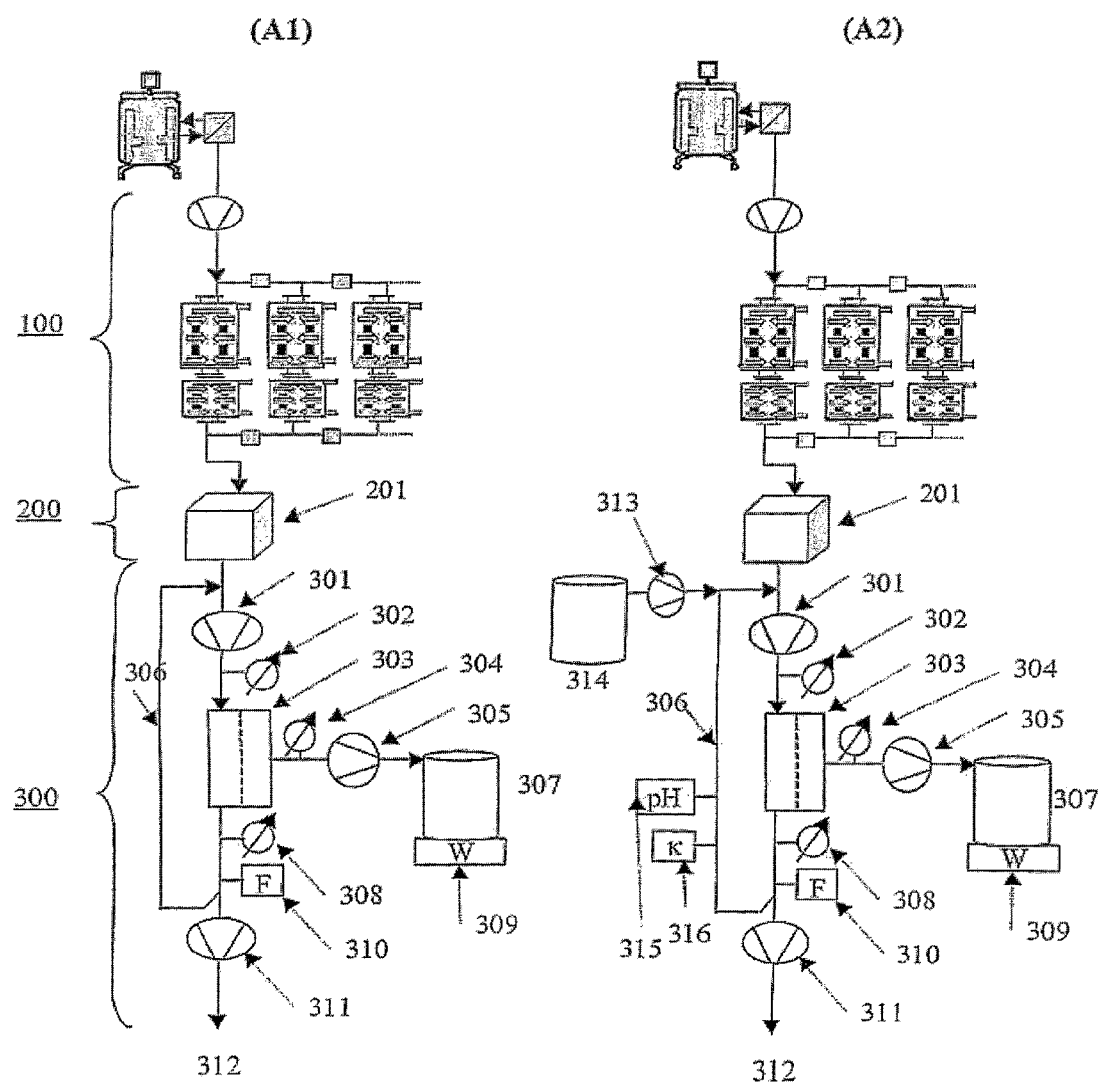
FIG. 2: Schematic representation of 2 embodiments of inventive device A for continuous, integrated and sterile manufacturing. Schematic of embodiment A1 shown on left hand side and schematic of embodiment A2 shown on right hand side.
Figure 3:
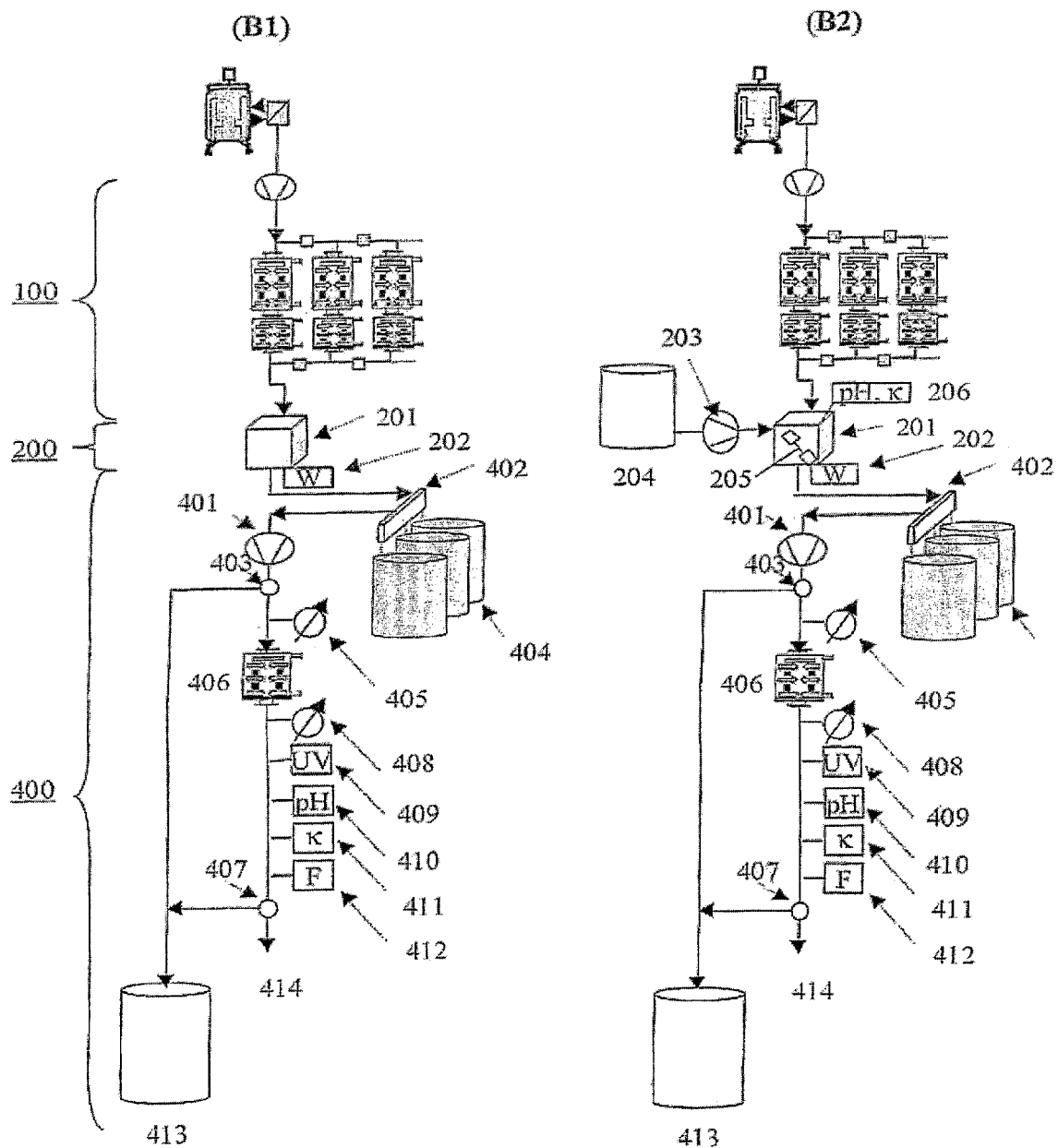
FIG. 3: Schematic representation of 2 embodiments of inventive device B for continuous, integrated and sterile manufacturing. Schematic of embodiment B1 shown on left hand side and schematic of embodiment B2 shown on right hand side.

To provide for integrated continuous or semi-continuous concentration/purification of the protein product, the inventive device A (of which two embodiments are shown in FIG. 2) comprises an integrated continuous, sterile ultrafiltration system (300), while inventive device B (of which 2 embodiments are shown in FIG. 3) comprises an integrated, semi-continuous convective adsorption/desorption system (400).

The devices of the invention are directly integrated with one or more continuous perfusion fermenter(s) and thus form a novel continuous, integrated manufacturing platform.

Device A
Integrated Continuous Particle Removal System (100)

FIG. 2 shows 2 embodiments of inventive device A. The integrated continuous particle removal system (100) is directly connected to the harvest side of the continuous perfusion fermentation system (1).

Figure 4:
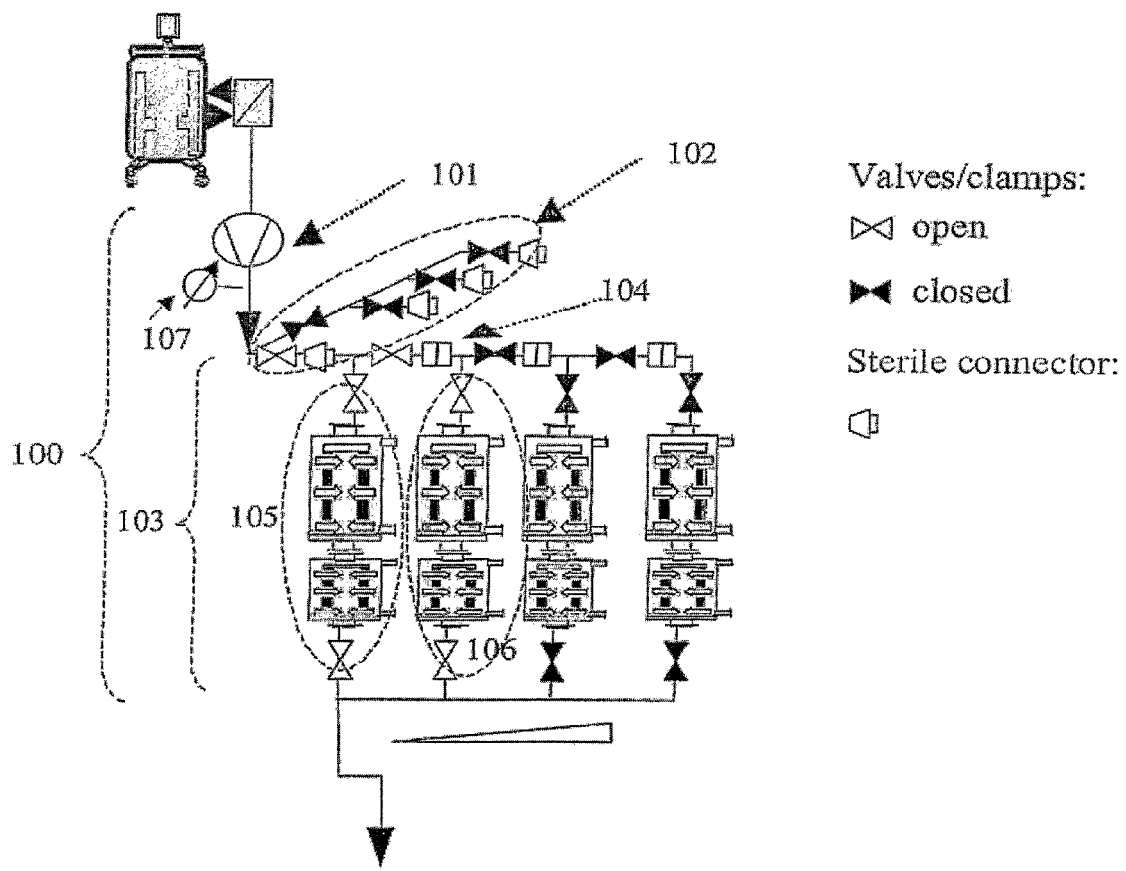
FIG. 4: Schematic of an embodiment of inventive integrated, continuous particle removal system (100), an element of both inventive device A and inventive device B.

FIG. 4 shows a more detailed schematic representation of an embodiment of the inventive integrated continuous particle removal system (100), which consists of a pump (101), a pressure gauge or transmitter, respectively (107), a connection manifold (102) and an assembly of several filter trains (103). All components are connected with flexible tubing and/or hard piping.

The pump (101) is a conventional peristaltic pump, which allows gentle pumping of the cell culture harvest without any rotating parts or seals contacting the sterile product. The pump and the pump tubing is sized to deliver the desired harvest flow rate of the cell culture fermentation system, which is up to 15 bioreactor volumes per day, e.g. up to 9.4 liters/hour for a 15 liter fermenter and up to 125 liters/hour for a 200 liter fermenter.

The pressure gauge or pressure transmitter (107) is designed such that it can be sterilized by autoclaving or irradiation. In the current design, either a re-usable piezoresitive transmitter in a stainless steel housing or a re-usable stainless steel pressure gauge are used. However, future improvements can include the use of disposable transmitters which can easily be sterilized by irradiation.

In a present embodiment the Connection manifold (102) consists of flexible tubing, with tubing clamps (or valves) and appropriate sterile connectors for allowing connection of additional filter train assemblies without compromising system sterility. Preferably, the tubing diameters are sized to yield linear fluid velocities of about 2 m/s or less at the desired flow rates, thereby avoiding high backpressures and shear. In another present embodiment, instead of the sterile connectors special flexible tubing pieces are used that can be welded with commercial tubing welders without compromising sterility. Such tubing pieces are made of polyvinyl chloride (PVC) or other suitable polymers.

The filter train assembly (103) consist of at least two, preferably multiple identical filter trains (as shown in schematic), with only one of the filter trains open at any given time, as shown as an example in the FIG. 4 (105).

Each filter train consists of at least one filter, preferably one pre-filter and one final filter in series (as shown in FIG. 4). If required to increase capacity for a specific application, each filter train (105, 106 etc.) itself can also consist of multiple filters or filter trains in parallel (not shown).

In an embodiment of the invention shown in FIG. 4, the second filter train of the assembly (106) is closed off by a pressure-sensitive rupture disc, or rupture pin, respectively (104). In operation, the function of the rupture disc, or rupture pin, is to automatically open up the flow-path to the second filter train (107) once the pressure in the first filter train (105) reaches a specified limit, thereby ensuring uninterrupted continuation of the filtration process. Commercially available rupture discs or rupture pins are utilized in the inventive system, which are otherwise used to provide safety pressure relief. In a present embodiment, rupture discs or rupture pins with a specified rupture pressure limit of not more than 16 pounds per square inch (PSI) are used, which has proven to be very useful. However, a range of specified pressure limit is possible.

Each further filter train of the filter train assembly is also separated by a manual or automatic valve and another rupture disc or rupture pin. Once the second filter train (106) is operational, the valve to the next rupture disc or rupture pin, respectively, is opened, so that the next filter train can act as a backup and so forth.

In an alternative embodiment, automatically actuated valves are used exclusively, and in operation, a control system actuates the valves based on the input of a piezoresitive pressure sensor (107) which can also be sterilized by autoclaving. However, applicants discovered that the present design comprising the rupture disc or rupture pin, respectively, provides outstanding robustness in long-term operation.

The final filter rating is at least 3 µm or smaller, preferably 0.45 µm and still preferably 0.2 µm. The operating filter train (6) therefore retains all remaining cells, as well as, relevant cell debris and other particles, resulting in a particle-free output stream (9), the clarified tissue culture fluid (cTCF).

Different commercially available filter materials can be used. In the current design, disposable filter capsules are used, such as Sartopure or Sartoclear pre-filter capsules (Sartorius, Goettingen) and Sartobran final filter capsules (Sartorius, Goettingen), which can be sterilized by autoclaving or irradiation.

As an example of a present embodiment of the inventive device, designed for a flow rate of 1 liter/min, each filter train (105, 106 etc.) of the assembly (103) consists of 3 30" pre-filter capsules (Kleenpak Ultipleat, Pall Corp., 4.5 um rated, 0.75 m$^2$ each) followed by 3 20" final filter capsules (Sartobran P, Sartorius, 0.45 um/0.2 um rated, 1.3 m$^2$ each). This particular embodiment has been found particularly useful for large-scale manufacturing of recombinant blood coagulation Factor VIII, as well as, genetically engineered FVIII variants including B-domain deleted FVIII.

However, applicants have discovered that when using inventive device and method, the efficiency of particle removal with a variety of available filter materials and configurations from different manufacturers (Pall, Sartorius, Cuno) is consistently and significantly improved compared to the respective conventional batch processes.

Therefore, the novel inventive device and process will also be beneficial for use with novel filter types and geometries, e.g. with filter types that increase available filter area per capsule, as well as, with filter types that provide a cross-flow pattern or other means to minimize cake built-up, such as vibration or filter element rotation.

In another embodiment of the inventive process, the filter train assembly (103) comprises only one sterile back up filter train closed by a rupture disc or rupture pin, respectively, but still multiple filter trains for operation. The first filter train of the assembly is operated until a specified pre-determined loading volume has been processed, after which operation is switched over (manually or automatic) to the next filter train in the assembly. The specific loading volume is specified so that under normal operating conditions the pressure limit of the rupture disc or rupture pin is not exceeded. If however the pressure increases more then usual during filtration, e.g. due to an unusually low filterability of the harvest, the back-up filter train ensures again uninterrupted continuous filtration by opening up once the specified pressure is exceeded. Following an opening of the back-up filter train, filtration is switched to another filter train of the assembly and another back-up filtration train with rupture disk or rupture pin is installed without compromising the sterility of the system.

It is well know to those knowledgeable in the field, that to keep both filter costs and processing times for batch particle removal processes at a minimum, batch filter trains need to be sized to have the lowest possible filter area required for providing the desired absolute flow rate (in liters/hour) and maximum pressure. The desired absolute flow rate in turn has to be high enough to provide feasible processing times for the desired batch volume. This inherently necessitates a high specific flow rate (in liters/hour/m$^2$ of filter area).

In contrast to a comparable optimized batch filtration system, the inventive device is designed for several fold lower specific flow rate, which is kept constant (in liters/hour/m$^2$ of installed filter area) so that the absolute flow rate is equal to the harvest flow rate of the continuous perfusion fermentation.

Applicants unexpectedly discovered that at such low specific flow rates the volume that can be processed through a filter is disproportionately higher than at the flow rates adjusted in batch processes.

It is important to note that in conventional batch isolation processes, such low specific flow rates would not be feasible due to either extreme filtration areas (and thus costs), or too low of an absolute flow rate. This is primarily because most of the time, the batch particle removal equipment sits idle while harvest is being collected for the next batch. Moreover, the surprising disproportionate increase in achievable filter capacity of the inventive method allows for a significant reduction in filter consumption and thus manufacturing costs.

Surge Vessel (200)

The outlet of the integrated continuous particle removal system is directly and constantly connected to a surge vessel (201), as shown in FIG. 2. This surge vessel is a sterile vessel, such as, a disposable bag or a stainless steel vessel with at least one inlet port and one outlet port, the later preferably on the bottom of the vessel. A broad range of vessel sizes and designs can be utilized. However, the surge vessel is preferably sized to be small compared to the volumetric throughput of the system to keep the residence time of the product in the vessel at a minimum, i.e. below 24 hours, preferably below 8 hours, and still preferably below 4 hours.

Applicants discovered that such low product residence times, uniquely possible due to the inventive devices, allow significant increase in yield for inherently unstable protein products, thereby solving one of the problems of the prior art.

In some embodiments of the inventive devices, the surge vessel is located on a balance or load cell (202), as shown for device B1 and B2 in FIG. 3. This balance or load cell provides a weight signal to a computerized control system (not shown).

In addition, in an embodiment of the inventive devices (B2), a buffer vessel (204) is connected via a peristaltic pump (203) to the surge vessel. In operation, this set-up is used to adjust the properties of the particle-free harvest stream, such as conductivity (ionic strength) or pH, by adding suitable buffer or diluent. In this case, an optional mixing system (205) and sensors to monitor the desired condition (206), such as pH or conductivity, are used. In the present design, a magnetically coupled stirrer is used; however, other mixing systems, such as shakers or pulsating devices could be used as well.

Integrated Continuous Concentration/Purification (300)

Device A, 2 embodiments of which are shown in FIG. 2, comprises an integrated continuous, sterile ultrafiltration system (300). Embodiments of the continuous, sterile ultrafiltration system comprise a recycle pump (301) and recycle loop (306), one or more sterile crossflow ultrafiltration modules (303), a permeate pump (305), a sterile permeate receiving vessel (307) on a balance or load cell (309) and a retentate pump (311). Furthermore, it comprises instrumentation in form of an inlet pressure gauge or transmitter (302), permeate pressure gauge or transmitter (304), outlet pressure gauge or transmitter (308), as well as, a recycle flow meter (310). In operation, the system outlet (312) provides a continuous stream of concentrated and partially purified protein product, which can be continuously collected, frozen or further processed.

Inventive embodiment A2 comprises in addition a buffer or diluent vessel (314), a peristaltic buffer/diluent addition pump (313), as well as, flow-through sensors to monitor conditioning of the concentrate in the recycle loop, such as sensors for pH and conductivity (315, 316). In operation, this set-up is used to adjust the properties of the particle-free harvest stream, such as conductivity (ionic strength) or pH, by adding suitable buffer or diluent. This set-up can also be used to add protein stabilizers. Although in inventive embodiment A2 the recycle loop itself acts as a mixing chamber, conditioning can alternatively also be performed by using a surge vessel set-up as shown for device B (embodiment B2), comprising components (203, 204, 205, 206) as discussed later in this disclosure (see description of device B).

Embodiments of the inventive device also comprise a datalogging and programmable control system, which records incoming data signals from the instrumentation (such as, but not limited to, pressures, flow rate, vessel weight, pH, conductivity) and controls the pump speeds according to a predefined control algorithm.

All pumps (301, 305, 311, 313) are peristaltic pumps, which allow pumping of the respective fluid streams without any rotating parts or seals contacting the sterile product stream. Applicants discovered that this is preferable to provide robust sterile long-term operation. However, other sterile pump designs can in principal be used. The recycle pump (301) and its pump tubing is sized to allow robust adjustment of the desired cross-flow rates of between 80 and 800 liters/hour per $m^2$ of installed membrane area, depending on the mass transfer characteristics of the ultrafiltration module used. The permeate pump is sized to allow robust and precise adjustment of a specific permeate flux of between 90% and 99% of the harvest flow rate from the continuous perfusion fermentation. The retentate pump is sized to allow a robust and precise adjustment of the retentate flow of between 1% and 10% of the harvest flow rate from the continuous perfusion fermentation.

Encapsulated ultrafiltration modules (303) are used to allow robust sterile operation, and are sterilized by autoclaving or irradiation. The optimal nominal molecular weight cut-off is chosen based on the molecular weight of the protein product of interest and has to be confirmed by standard experiments known to those in the art. A variety of membrane materials, such as polyethersulfone, hydrophilized polyethersulfone or regenerated cellulose can be used, as long as the entire membrane module can be sterilized by irradiation and/or autoclaving without damaging the membrane. It is expected that hydrophilic materials can increase efficiency due to their lower fouling tendencies.

Applicants discovered, that device A is uniquely efficient if the installed total ultrafiltration membrane area in square meters is equal to a range of between 0.1 to 2 times the volumetric flow rate of the harvest from the continuous perfusion fermentation in liters/hour. E.g. for a perfusion harvest flow rate of 1 liter/hour, the installed total membrane area should be between 0.1 and 2 square meters. Applicants discovered that the device A is yet more efficient, if the installed ultrafiltration membrane area in square meters is equal to a range of between 0.3 to 1 times the volumetric flow rate of the harvest from the continuous perfusion fermentation in liters/hour.

In one embodiment of the invention, commercially available "disposable" hollow fiber membrane modules (GE Healthcare, former Amersham Biosciences) are used. However, a variety of encapsulated membranes and module designs can be used, such as spiral wound modules, encapsulated cassettes or capsules with enhanced mass transfer due to secondary flow patterns (e.g. vortex flow), rotating elements (e.g. dynamic disk filters) or vibrating filters. It is expected that especially encapsulated ultrafiltration cassettes can be used beneficially in the inventive devices since they provide high mass transfer coefficients at relatively low required cross-flow rate, thereby reducing pump capacity, while keeping system complexity and investment costs low.

The inventive device allows not only continuous, but also truly sterile operation, in contrast to just aseptic operation. Applicants achieved this by designing all product-contacting system components to withstand not only cleaning, but also sterilization by autoclaving, steaming in place or gamma-irradiation. In present embodiments disposable encapsulated modules are used for continuous particle removal (100), as well as, continuous ultrafiltration (300). Peristaltic pumps are used to avoid any product contact with rotating elements and mechanical seals. Moreover, in present embodiments disposable tubing and bag assemblies are used instead of hard piping. Disposable product contacting components (e.g. tubing, bags, modules) or component groups are pre-assembled and sterilized together, thereby simplifying start-up and operation. The systems are designed to keep any potential opening of the sterile system to the environment (e.g. laminar flow hood), as for sampling, bag or instrumentation exchange to a minimum. In present embodiments of the device, manifolds are designed redundant to allow switching from one sterile component (e.g. product receiving bag) to the next without opening. Additional exchange of tubing, modules or bags is preferably performed by using sterile tubing welders rather then sterile connectors.

Other future embodiments of inventive devices could also comprise components such as stainless steel vessels, filter housings or piping that can be sterilized in place, alone or in combination with disposable components, as long as robustness and sterility in long-term operation is assured.

Figure 5:
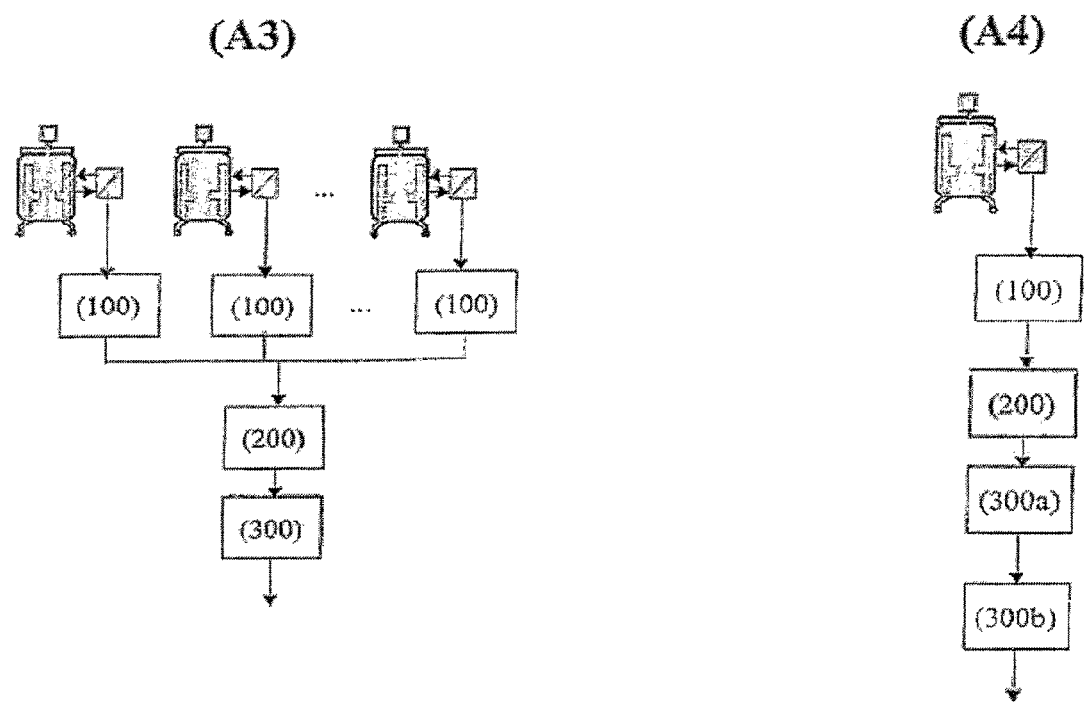
FIG. 5: Schematic representations of additional embodiments of inventive device A which combine multiple elements to either increase overall plant capacity (A3) or concentration and separation performance (A4).

Additional embodiments of inventive device A are designed to process material from multiple fermenters in larger manufacturing plants (A3). An example is shown schematically in FIG. 5. Further embodiments are designed to increase the overall concentration factor and separation performance by combining 2 stages of continuous ultrafiltration systems (300) in series (A4, shown schematically in FIG. 5).

Description of Method of Using Device A

The continuous perfusion fermentations are operated over a long period of time (one campaign), typically between 2 weeks and 6 months or more. The tissue culture fluid (TCF) containing product, cells and cell-debris is continuously processed using the device A. A sterile, particle-free, concentrated and partially purified product stream (the "product isolate") is produced and continuously leaves the device at its outlet (312). By using the pump (101) of the continuous, sterile particle removal system (100) the harvest is pumped continuously through the filtration assembly (103) at the desired perfusion harvest flow rate Qh of the fermentation.

The output stream of the continuous filtration system, i.e. the clarified tissue culture fluid (cTCF), continuously enters the surge vessel (201). From the surge vessel the cTCF is continuously processed by a continuous, sterile ultrafiltration system (300) at a flow rate equal to the flow rate coming from the continuous perfusion fermentation. Due to the small sizing of the surge vessel relative to the adjusted flow rates, the mean residence time of the product in the vessel is kept at a minimum, i.e. below 12 hours, preferably below 4 hours and still preferably below 2 hours.

Adequate crossflow and thus mass transfer is adjusted in the ultrafiltration module via the recycle pump (301). The retentate flow rate is adjusted and controlled by using the retentate pump (311), thus yielding a constant and continuous flow rate Qi of the concentrated product isolate leaving device A at it's outlet (312). The permeate pump (305) is used to adjust and control the flow rate Qp of the permeate, which is drawn continuously from the permeate side of the ultrafiltration module(s), and which consists of water and solutions components small enough to pass through the ultrafiltration membrane (e.g. salts, small proteins).

The flow rates of permeate (Qp) and retentate/isolate (Qi) are carefully adjusted and controlled to match the harvest flow rate Qh of the fermentation so that:

$$Qp+Qi=Qh$$

At the same time, the flow rates are adjusted and controlled so that a desired concentration factor cf is achieved by satisfying:

$$Qi=1/cf*Qh$$

For example, to achieve a desired product concentration factor of 10 fold in the isolate over the initial harvest concentration, Qi is controlled at $Qi=1/10*Qh$ using the retentate/isolate pump (311), while Qp is controlled at $Qp=0.9*Qh$ using the permeate pump (305).

Since outflow rates are controlled by the pumps (305) and (311), the ultrafiltration system automatically draws a flow of Qp+Qi from the small surge vessel (201).

In case of using embodiment A2 (see FIG. 2 right hand side), a sterile stream of buffer or water for injection from vessel 314 is added to the continuous ultrafiltration system continuously at a constant flow rate Qb using the buffer addition pump (313). Therefore, the conditions of the isolate can be freely and continuously adjusted, e.g. in terms of ionic strength, pH, addition of stabilizers, etc. Flow rates are therefore controlled at $$Qp+Qi=Qh+Qb$$

Furthermore, flow rate ratios can be chosen so that a desired concentration factor cf is achieved by satisfying $Qi=1/cf*(Qh+Qb)$. Alternatively, this process can be used to only alter conditions (e.g. pH, conductivity), by setting $Qi=Qh+Qb$.

Figure 9:
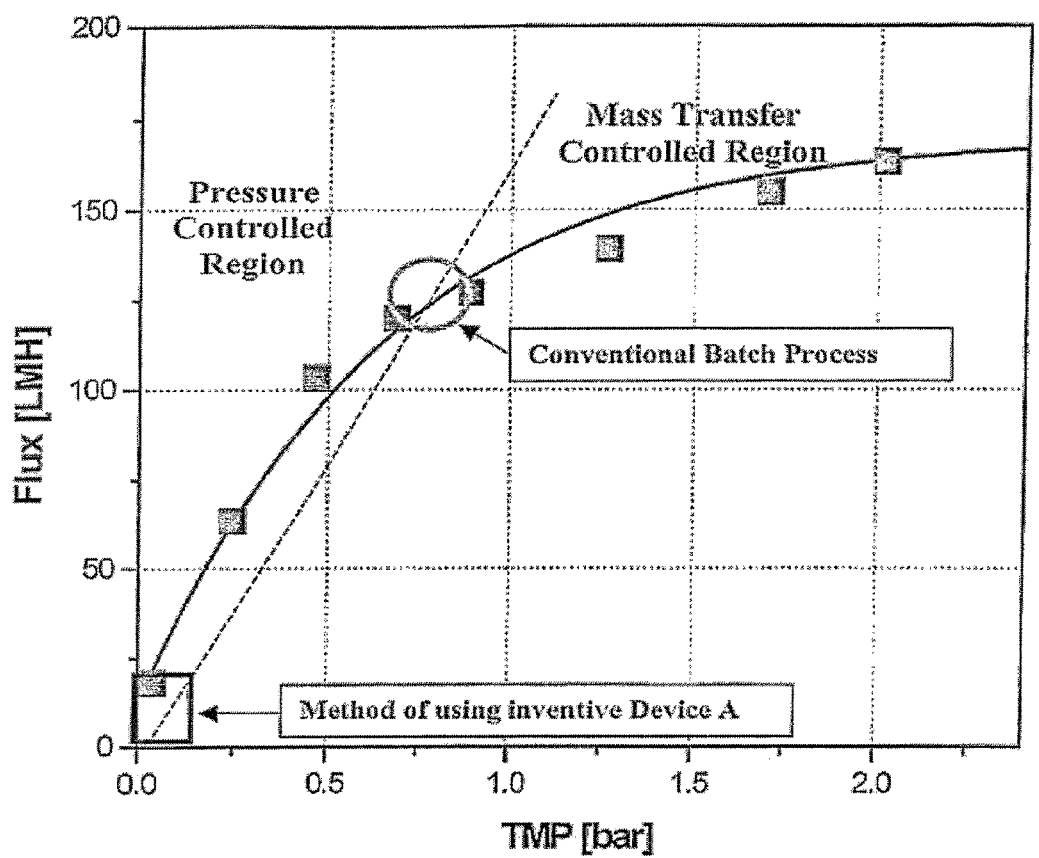
FIG. 9: Example of pressure-flux curve (specific permeate flux in LMH=liters/hour/m$^2$ over transmembrane pressure) and determination of operation point. The circle shows the typical operation point that will be adjusted via the TMP for conventional batch processes. The rectangle shows the preferred operational region that will be adjusted via the permeate pump as per the method of using the inventive device A.

The novel method of using device A also contrasts with the UF batch processes (prior art) in terms of the operational set-point of the ultrafiltration itself. Conventional Batch UF processes are designed for a certain throughput through a low membrane area in a short period of time. Batch UF is thus generally operated at the transition point of pressure dependent to mass transfer controlled region (see FIG. 9). This leads to a desirably high initial specific flux, which however drops significantly and rapidly over the course of seconds to minutes, as concentration polarization leads quickly to osmotic back-pressure and the formation of a limiting gel layer (secondary membrane). Such a high wall concentration of macromolecules also leads to an increased adsorption of compounds to the inner and outer membrane surface, i.e. to membrane fouling. This fouling would further reduce the permeate flux over time.

Applicants surprisingly discovered that with device A, many times higher overall loading capacities per area of installed ultrafiltration membrane are achieved by operating at the low end of the pressure-flux curve (see FIG. 9):

The normalized wall concentration cwall of a fully retained component can be described as follows:

$$c_{wall} = e^{\frac{J}{k_d}} \cdot c_{bulk}$$

with
J=specific permeate flux in liters/hour/m2
kd=mass transfer coefficient in liters/hour/m2
cbulk=concentration of the component in the solution bulk Like in batch UF, the continuous UF is operated at optimized mass transfer coefficient to minimize concentration polarization. However, in contrast to batch ultrafiltration, applicants adjust the permeate flux J to be at the low end of the pressure-flux curve (see FIG. 9). As a result of the exponential relationship, the wall concentration cwall at the surface of the membrane is therefore significantly lower than it would be in batch ultrafiltration. For example, the present embodiment of the inventive method adjusts a target specific permeate flux of approximately $\frac{1}{10}$ of the achievable mass transfer coefficient, thereby adjusting a wall concentration of only 10% above the adjusted bulk (or retentate) concentration.

The following Table 1 shows an example of a method for using device A (embodiment A1) for continuous isolation of a protein product from a development scale fermenter:

TABLE 1

Example of method for using a present embodiment of device A for continuous isolation of a protein product from continuous perfusion fermentation

| Operational Parameter | Target |
|---|---|
| Harvest flow rate Qh from continuous perfusion (controlled with pump 101) | 5 liters/hour (120 liters/day) |
| Permeate flow rate QP (controlled with pump 305) | 4.75 liters/hour |
| Retentate (product isolate) flow rate Qi (controlled with pump 311) | 0.25 liters/hour |
| Specific permeate flux J | 2 liters/hour/m2 |
| Concentration factor cf | 20 fold |

For each individual product molecule, a lifetime criteria can be defined for the sterile continuous ultrafiltration set-up, e.g. based on trans-membrane pressure. Once the trans-membrane pressure limit is exceeded, the continuous sterile ultrafiltration set-up is exchanged against another identical set-up without compromising integrity and sterility of the system. This can be done in analogy to the continuous, sterile filtration set-up by using either manifolds and sterile connectors, or by using disposable flexible tubing and sterile tubing welders.

Device B
Integrated Continuous Particle Removal System (100)

FIG. 3 shows 2 embodiments of inventive device B. The integrated continuous particle removal system (100) is directly connected to the harvest side of the continuous perfusion fermentation system (1). This part of device B is identical to device A (see detailed description of device A and FIG. 4, above).

Surge Vessel (200)

The outlet of the integrated continuous particle removal system is directly and constantly connected to a surge vessel (201), as shown in FIG. 3. This surge vessel is a sterile vessel, such as, a disposable bag or a stainless steel vessel with at least one inlet port and one outlet port, the later preferably on the bottom of the vessel. A broad range of vessel sizes and designs can be utilized. However, the surge vessel is preferably sized to be small compared to the volumetric throughput of the system to keep the residence time of the product in the vessel low, i.e. below 26 hours, preferably below 12 hours and still preferably below 4 hours.

In device B, the surge vessel is located on a balance or load cell (202), as shown for embodiments B1 and B2 in FIG. 3. This balance or load cell provides a weight signal to a computerized control system (not shown).

In addition, in an embodiment of the inventive device (B2), a buffer vessel (204) is connected via a peristaltic pump (203) to the surge vessel. In operation, this set-up is used to adjust the properties of the particle-free harvest stream, such as conductivity (ionic strength) or pH, by adding components for modifying the properties of the clarified tissue cultured received from the particle removal system, such as a suitable buffer or diluent, or a suitable protein stabilizer. In this case, a present embodiment also comprises a mixing system (205) and sensors to monitor the desired condition (206), such as pH or conductivity, are used. In this present embodiment, a magnetically coupled stirrer is used; however, other mixing systems, such as shakers or pulsating devices could be used as well.

In another embodiment of the inventive device, 2 surge vessels are used. At any given time, one surge vessel is directly connected to the continuous particle removal system (100), thereby receiving clarified fluid, while the other one is connected to the semi-continuous concentration/purification system (400), thereby feeding a convective adsorption/desorption cycle. Switching between both is realized through a control system, using the weight of the receiving vessel to trigger a switch once its maximum filling volume is reached.
Integrated Semi-Continuous Concentration/Purification (400)

Device B, 2 embodiments of which are shown in FIG. 3, comprises an integrated semi-continuous, convective adsorption/desorption system (400).

The integrated semi-continuous convective adsorption/desorption system is designed and sized so that its loading flow rate (Qload) is significantly higher than the flow rate of the continuous perfusion harvesting and continuous filtration process (Qh), i.e. Qload>>Qh.

Embodiments of the integrated semi-continuous concentration/purification system (400) comprise a load pump (401), a multi-port valve assembly (402) and several buffer vessels (404), a 3-way-valve (403) connected to a sterile waste receiving vessel (413) and one or more convective adsorber module(s) (406), inlet- and outlet-pressure gauges or transmitters (405, 408), further instrumentation such as UV sensor (409), pH and conductivity sensors (409, 410), flow meter (412), as well as, another 3-way valve (407) connected also to the waste vessel (413) and the product eluate outlet (414).

Embodiments of the inventive device also comprise a datalogging and programmable control system (not shown), which records incoming data signals from the instrumentation (such as, but not limited to, pressures, UV, pH, conductivity, flow rate, surge vessel weight) and controls the automated valves and pump according to programmed protocols.

The load pump (401) is preferably a peristaltic pump to avoid direct contact of product or sterile buffers with any seals or mechanical parts. Applicants discovered that this is preferable to provide robust sterile long-term operation. However, other sterile pump designs can in principal be used. The load pump is sized depending on the installed matrix volume of the convective adsorber (406) to allow robust adjustment of at least 12 matrix volumes/minute. E.g., in one present embodiment, Mustang membrane adsorber capsules (Pall Corp.) are used that have a matrix volume of approx. 0.3 liters. Therefore, the load pump is sized to allow loading flow rates of up to 3.6 liters/minute.

The function of the multi-port valve assembly (402) is to allow switching between the product containing load drawn from the surge vessel (201) and each of the sterile buffers and cleaning solutions from the sterile buffer vessels (404). Present embodiments of device B utilize a series of automatically actuated pinch valves, which pinch the flexible tubing connected to each buffer vessel from the outside to close of and open each line. Applicants discovered that these pinch valves provide a particularly beneficial solution for device B since they avoid any product contact and thus do not need to be cleaned or sterilized. However, a wide range of commercial valves suitable for sterile processing and known to those familiar with the field can be used, such as actuated membrane valves.

In the present embodiment, the 3-way valves (403, 407) are autoclavable actuated membrane valves. However, a variety of commercial valves suitable for sterile processing can in principal be used, including e.g. pinch valves.

The convective adsorber module (406) contains a chromatographic matrix with pre-dominantly convective mass transfer of the product to the adsorptive surface and, in contrast to conventional chromatography, is sterilized prior to operation by autoclaving, steaming or irradiation. The pre-dominantly convective mass transfer allows, in contrast to conventional packed bed chromatography, very low adsorption/elution/regeneration cycle times, which applicants utilize in inventive device to realize semi-continuous operation.

In the present embodiment of the inventive device, the convective adsorber (406) consists of one or more commercially available membrane adsorber capsule(s) with ion exchange chemistry (Mustang, Pall corporation or Sartobind, Sartorius). However, the device can utilize other membrane adsorber materials and geometries and novel convective matrices such as monolithic matrices as well, since in contrast to conventional chromatography resin packing is eliminated and matrices can generally be encapsulated in ready-to-use modules.

Moreover, other chemistries, including convective affinity matrices comprising specific product-binding ligands will also yield uniquely beneficial performance in the inventive device.

In one embodiment of the inventive device, multiple convective adsorber modules are used in the device in form of an assembly of convective adsorber-trains in parallel, similar to the continuous particle removal system (100). The entire assembly with all adsorber-trains is sterilized together, allowing in operation switching from one adsorber-train to a fresh one should the first one reach the end of its useful life, as determined e.g. by a pre-defined criteria such as back-pressure during loading or maximum number of performed operating cycles. Each adsorber-train consists of either one individual module or multiple convective adsorber modules in parallel and/or in series to increase binding capacity and/or improve capacity utilization.

It is important to emphasize that the inventive device allows not only continuous, but also truly sterile operation in contrast to just aseptic operation. Applicants achieved this by designing all product-contacting system components to withstand not only cleaning, but also sterilization by autoclaving, steaming in place or gamma-irradiation. In present embodiments disposable encapsulated modules are used for continuous particle removal (100), as well as, semi-continuous sterile convective adsorption/desorption (400). Peristaltic pumps are used to avoid any product contact with rotating elements and mechanical seals. Moreover, in present embodiments disposable tubing and bag assemblies are used instead of hard piping. Disposable product contacting components (e.g. tubing, bags, modules) or component groups are pre-assembled and sterilized together, thereby simplifying start-up and operation. The systems are designed to keep any potential opening of the sterile system to the environment (e.g. laminar flow hood), as for sampling, bag or instrumentation exchange to a minimum. In present embodiments of the device, manifolds are designed redundant to allow switching from one sterile component (e.g. product receiving bag) to the next without opening. Additional exchange of tubing, modules or bags is preferably performed by using sterile tubing welders rather then sterile connectors.

Other future embodiments of inventive devices could also comprise components such as stainless steel vessels, filter housings or piping that can be sterilized in place, alone or in combination with disposable components, as long as robustness and sterility in long-term operation is assured.

Figure 6:
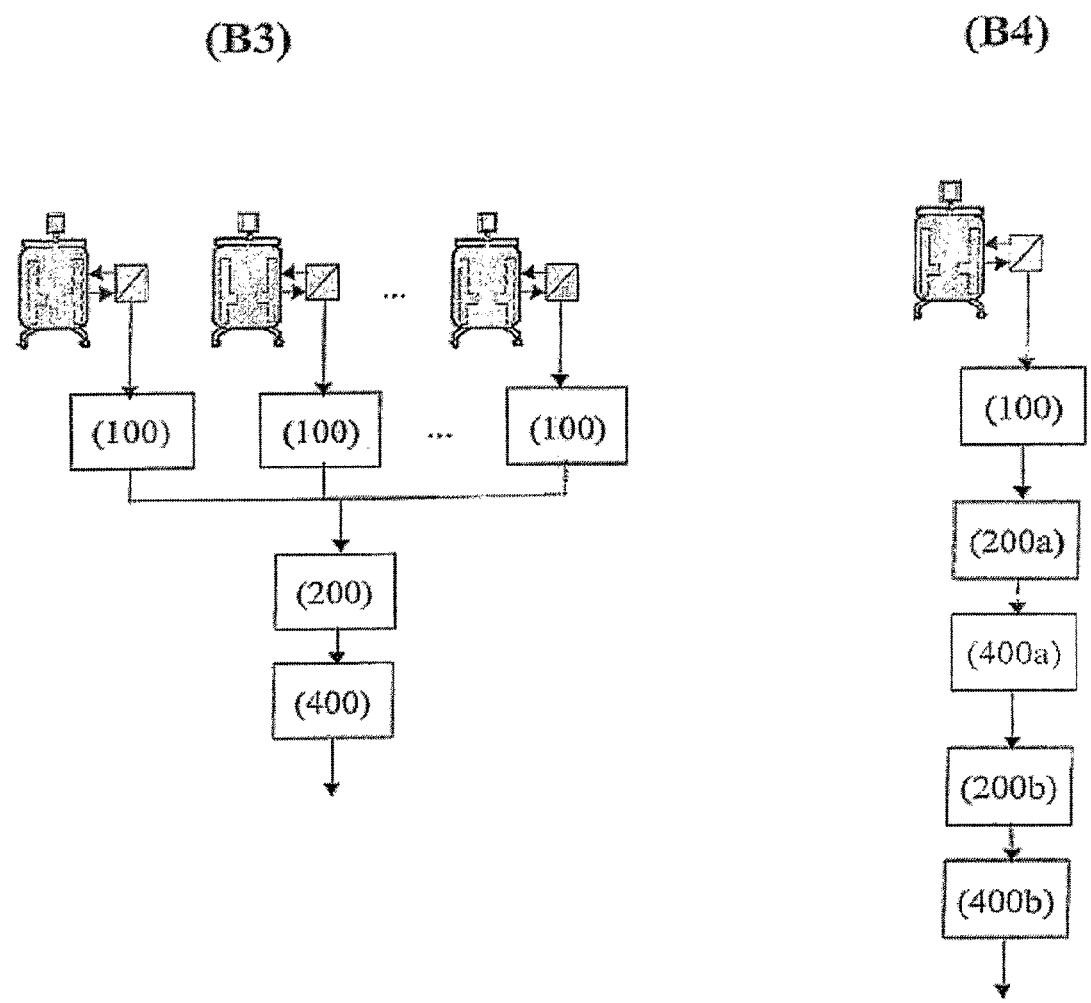
FIG. 6: Schematic representations of additional embodiments of inventive device B.

Additional embodiments of inventive device B are designed to process material from multiple fermenters in larger manufacturing plants (B3). An example is shown schematically in FIG. 6. Further embodiments of inventive device B are designed to increase the overall concentration factor and separation performance by combining multiple convective adsorption/desorption systems (400) in series, with respective sterile surge vessels in between (200) (see FIG. 6, B4).

Figure 7:
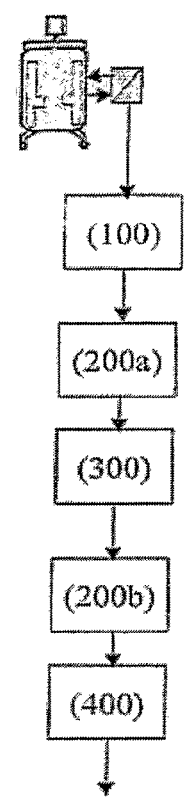
FIG. 7: Additional embodiment of inventive devices that combines the elements of device A and device B in series to increase overall concentration and separation performance.

Yet further embodiments of inventive devices are designed to increase the overall concentration factor and separation performance by combining a continuous ultrafiltration system (300) in series with a semi-continuous convective adsorption/desorption system (400) via an additional surge vessel. An example of an embodiment is shown schematically in FIG. 7.

Description of Method of Using Device B

The continuous perfusion fermentations are operated over a long period of time (one campaign), typically between 2 weeks and 6 months or more. The tissue culture fluid (TCF) containing product, cells and cell-debris is continuously processed using the device B. A sterile, particle-free, concentrated and partially purified product stream (the "product isolate") is produced and continuously leaves the device at its outlet (414). By using the pump (101) of the continuous, sterile particle removal system (100) the harvest is pumped continuously through the filtration assembly (103) at the desired perfusion harvest flow rate Qh of the fermentation.

The output stream of the continuous filtration system, i.e. the clarified tissue culture fluid (cTCF), continuously enters the surge vessel (201).

Whenever the surge vessel is filled to a pre-defined level, a weight or level signal triggers automatically an adsorption/desorption cycle of the integrated, sterile semi-continuous concentration/purification system. The material collected in the surge vessel is loaded rapidly onto the adsorber set-up, i.e. within 4 hours, preferably within 2 hours, and still preferably within 1 hour or less, thus emptying the surge vessel.

In the present embodiments shown in FIG. 3, collection of the particle-free clarified tissue culture fluid (cTCF) continues at all times, in the same small surge vessel. The volume in the small surge vessel therefore varies between a minimum and maximum value. In another embodiment described in the text before, collection is switched back- and forth between 2 identical surge vessels.

While cTCF is continuing to collect in the surge vessel, the loaded adsorber undergoes more steps of a pre-defined chromatographic protocol, designed to desorb the target product in concentrated, purified form and to ready the adsorber for the next loading cycle. Thus, the overall cycle comprises loading, wash, elution, regeneration and reequilibration, each with one or more suitable buffers.

Since again flow rates during these steps can be high due to the nature of convective adsorbers, total cycle time is kept low, i.e. below 6 hours, preferably below 3 hours and still preferably below 1.5 hours. Therefore, the integrated system is designed so that the adsorber set-up is ready for the next loading cycle before the surge vessel is filled again, thus allowing semi-continuous operation.

The following Table 2 shows an example of a method of using a present embodiment of the inventive device B for isolation of recombinant human blood-coagulation Factor VIII (large scale data shown). The method proved uniquely beneficial. Yields and performance of each adsorption/desorption cycle was similar to batch, with the overall product yield increased by more than 10% due to the lower residence time of the product and thus minimized product degradation. The same method has also proven to be very beneficial for the isolation of genetically engineered FVIII variants, including B-domain deleted FVIII, which is significantly different from full-length FVIII in size and other characteristics. It is expected to be useful for production of other proteins and biomolecules as well.

The chromatographic protocol itself (buffer chemistries & sequence, loading volumes and flow rates) can be developed in batch chromatography experiments for each individual molecule and can then be readily transferred to be used with embodiments of the inventive device.

TABLE 2

Example of method for using a present embodiment of device B for continuous isolation of FVIII and FYIII variants from continuous perfusion fermentation

| Parameter | Target |
| --- | --- |
| Harvest rate flow rate Qh of continuous perfusion [l/d] | 2000 |
| Surge vessel: max working volume Vs [l] | 200 |
| Loading volume [Matrix volumes] | 600 |
| Adsorber matrix volume installed in device B [ml] | 260 |
| Loading flow rate [Matrix volumes/min] | 12 |
| Loading volume [l] | 156 |
| Load time [min] | 50 |
| Total chromatographic time [h](protocol comprising load, wash, elution and several regeneration/reequilibration steps) | 1.5 |
| Idle time of adsorber/cycle [h] | 0.372 |
| Cycles/24 hour period | 12.8 |
| Collection time [h] | 1.872 |
| Approx. mean product residence time in device (collection time + load time + elution time) | 2.7 |

For each individual product molecule, a lifetime criteria is defined for the convective adsorber set-up, e.g. based on pressure during loading, or recovery. Typically, a maximum number of cycles nmax is specified and validated. Once the adsorber set-up has been used in semi-continuous operation through nmax cycles, it is exchanged against another identical adsorber set-up without compromising integrity and sterility of the system. In present embodiments this is done in analogy to the continuous, sterile filtration set-up by using either manifolds and sterile connectors, or by using disposable flexible tubing and sterile tubing welders.

When using the embodiment of the inventive device shown in FIG. 3, right hand side, a sterile stream of buffer, pH adjustment solution, stabilizer solution or water for injection is added either continuously or intermittently from a sterile vessel (204) using a buffer addition pump (203). Therefore, the conditions of the cTCF can be freely adjusted, e.g. in terms of ionic strength, pH, addition of stabilizers etc.

Benefits of Invention

The inventive devices and respective methods of using the devices solve the problems of conventional isolation processes outlined before (see general background of the invention).

In all embodiments of devices A and B and respective methods of using the devices, product residence time in potentially detrimental milieu is uniquely minimized, which significantly increases yield and quality of inherently unstable complex biological products. Plant capacity can be increased and cost of goods reduced.

Moreover, the devices and respective methods eliminate the need for large cold room facilities or cooled vessels for intermediate storage of large harvest volumes, thereby reducing plant investment costs and fully realizing the compactness and mobility advantage of perfusion fermentation.

Embodiments of both inventive devices and respective methods reduce labor costs compared to conventional, labor-intensive batch processing due to the inherently high degree of automation. The novel devices allow continuous operation, 24 hours a day, over long periods of time, maximizing volumetric throughput and equipment utilization.

Furthermore, inventive devices eliminate logistical difficulties in plants of one or multiple fermenters. Embodiments can process material from either one or multiple continuous perfusion fermentations.

Importantly, since the novel devices and methods allow completely sterile operation, microbial load issues, as well as, endotoxin issues are eliminated, which could not be achieved by aseptic processing followed by simple sterile filtration.

In addition, inventive devices enable avoiding or minimizing the need for cleaning validation due to the utilization of disposables. Through the unique characteristics of the inventive devices and methods, disposable modules, as well as, tubing, bags and assemblies can be used each for a long period of time (up to the entire length of the campaign), thereby dramatically lowering costs and making the utilization of disposables highly attractive from an economic standpoint.

Present embodiments of inventive devices A and B and respective methods have proven to be especially useful for manufacturing of recombinant blood coagulation Factor VIII, as well as, genetically engineered versions of FVIII including, but not limited to, B-domain deleted FVIII. However, the inventions can clearly be expected to be similarly useful for the production of other proteins and biological molecules, in particular complex inherently unstable proteins such as Factor VII, Factor IX, Factor X, and others.

Benefits of Device A and Respective Method

Figure 8:
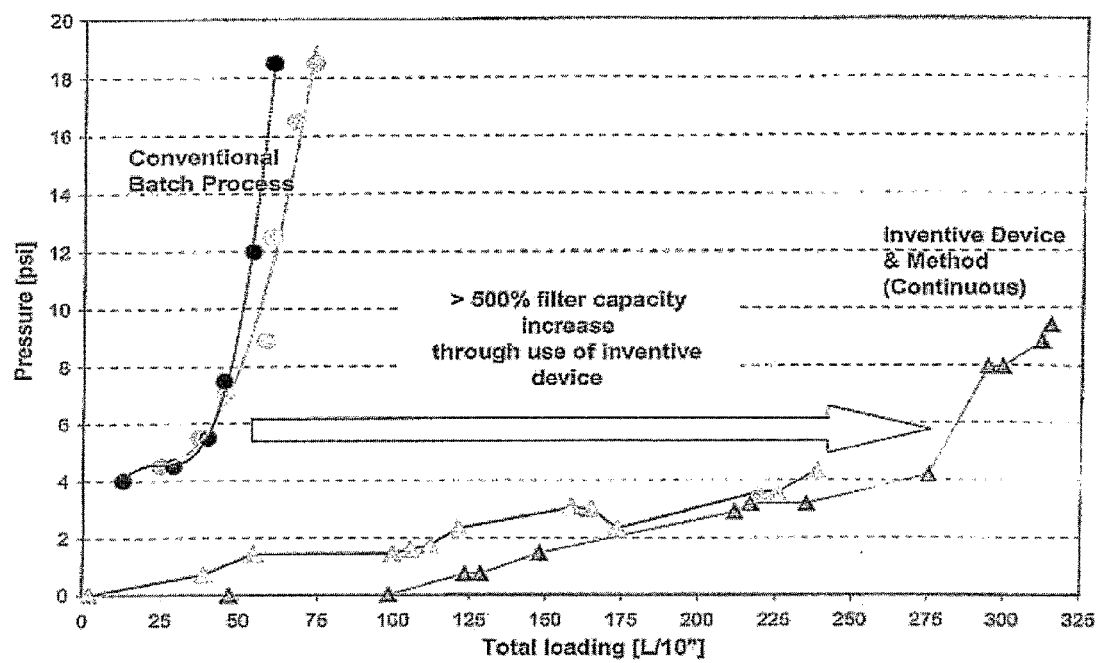
FIG. 8: Example comparison of total load capacities per 10" of filter capsule for conventional batch process and embodiment of inventive device and method for continuous particle removal (integrated continuous filtration process) using identical commercial filter capsules. Example method producing recombinant blood coagulation Factor VIII shown.

FIG. 8 shows an example of the surprising filter capacity increase applicants discovered for the integrated continuous particle removal element (100).

Figure 10:
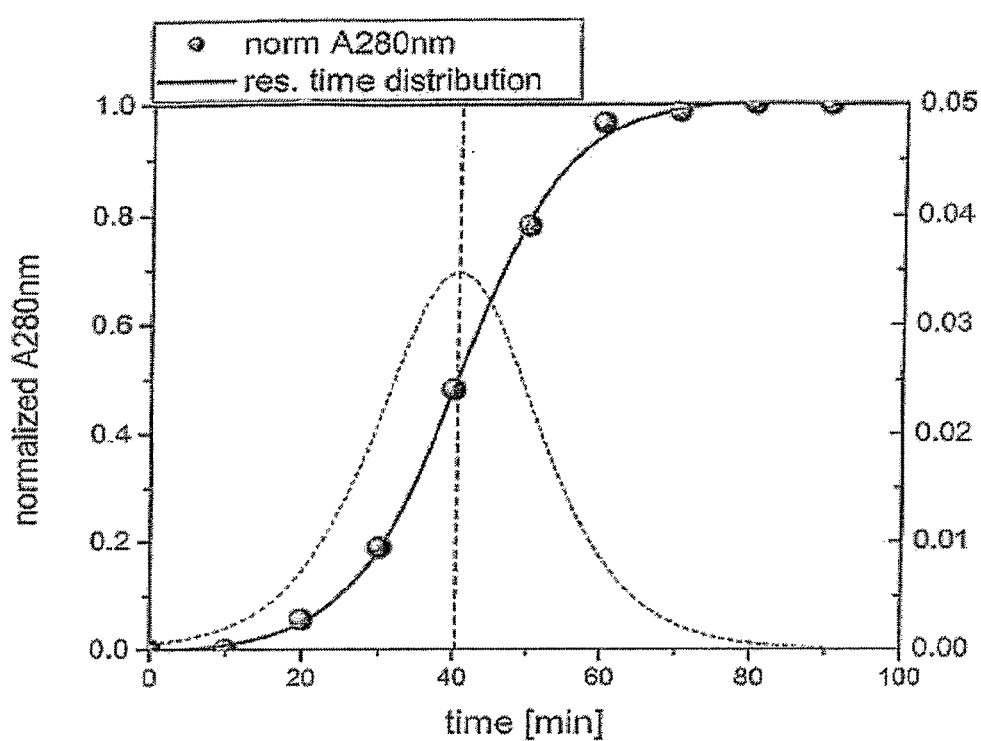
FIG. 10: Example of residence time distribution and mean residence time of integrated continuous UF system (300) as per method of using inventive device A. Measured for disposable continuous system with 290 cm2 module (62.5 cm length), 120 LMH crossflow, 0.2 LMH retentate flow, 2 LMH permeate flow.

FIG. 10 shows a typical residence time distribution and mean residence time of the product in the continuous UF system (300) of an embodiment of inventive device A, as determined by UV adsorption of the retentate at 280 nm, with a model protein under typical conditions. As can be seen, the mean residence time of the product in the system is only approximately 40 minutes. Therefore, the total residence time of the product in this present embodiment of device A, from fermenter harvest line to the final, concentrated retentate (isolate) is kept within 1-2 hours or less. This is less then ¹/₁₀ of the residence time of 28 hours or more in a conventional batch isolation process, in which the product (harvest) is collected for at least 24 hours (to several days), after which the product is processed for typically at least 4-10 hours.

Figure 11:
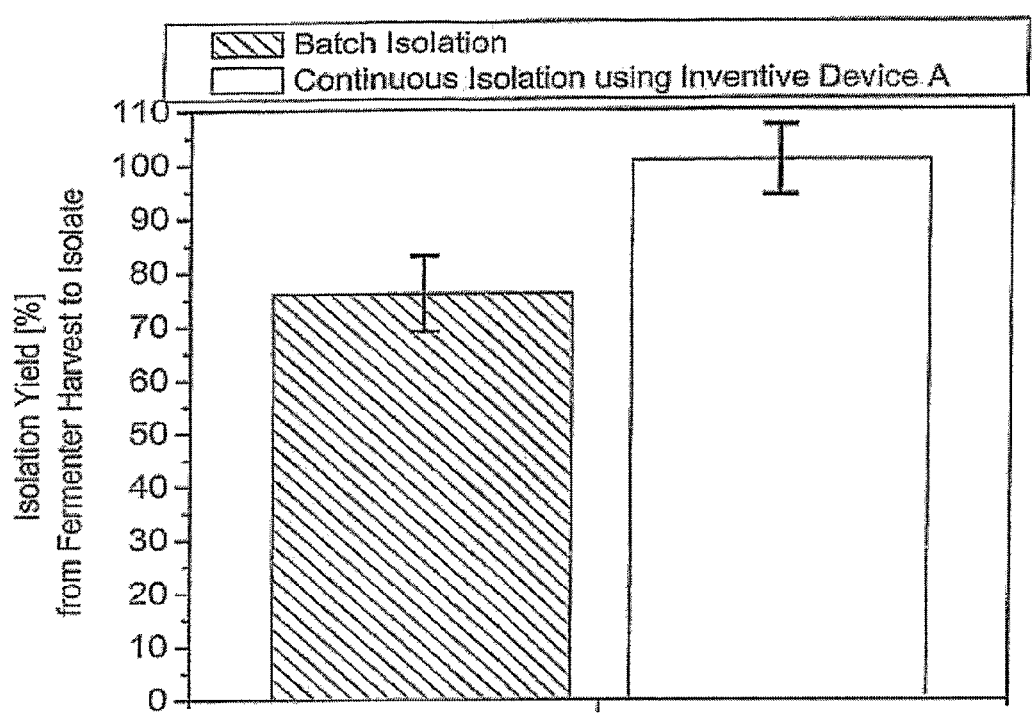
FIG. 11: Example of isolation of rFVIII from plasma-protein free continuous perfusion fermentation using an embodiment of inventive device A. Comparison of average isolation yield of inventive continuous method compared to average yield of batch isolation, including one standard deviation spread. 3 consecutive batches were used for determining batch yield, while 3 consecutive points (days) were used for the continuous process.

FIG. 11 shows a comparison of the resulting total isolation yields of recombinant blood coagulation factor (rFVIII) from plasma-protein free continuous perfusion fermentation for both a conventional batch isolation process (batch filtration plus batch UF) and using the inventive device A and respective method. As can be seen from the figure, the inventive continuous process achieves significantly higher product yield, which can lead to increased manufacturing capacities and reduced manufacturing costs.

Figure 12:
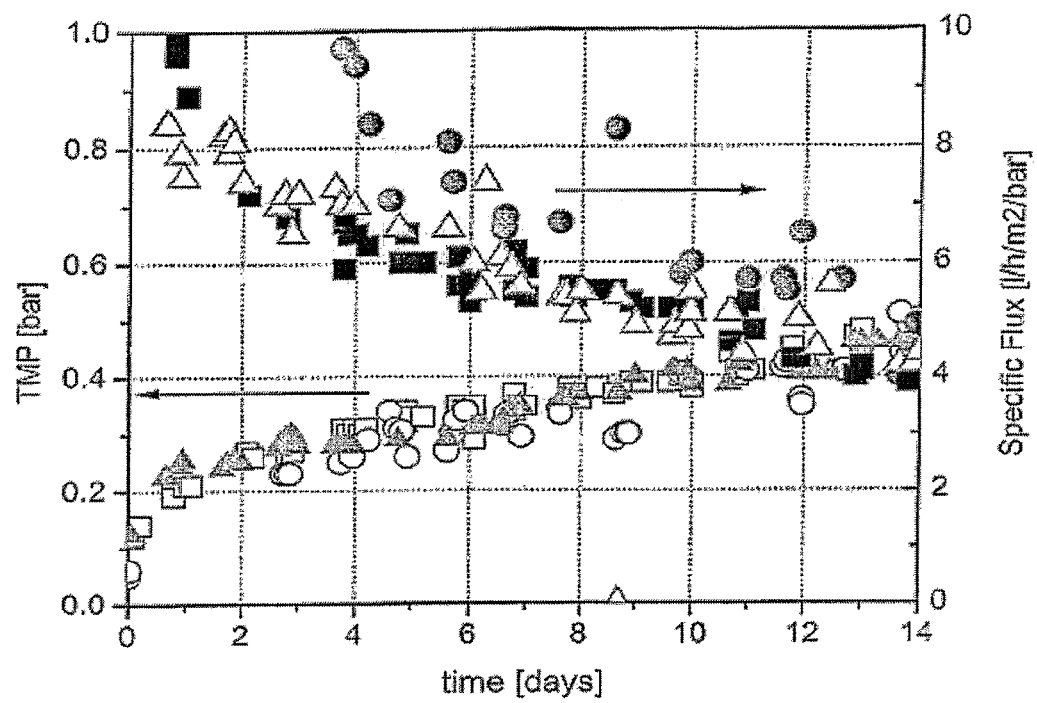
FIG. 12: Examples of performance of inventive device A. Transmembrane pressure and specific flux of integrated continuous ultrafiltration system (300) as a function of continuous process time for 3 different examples shown. Triangles=100 kD membrane, recombinant blood coagulation Factor VIII (rFVIII); Squares=10 kD membrane, recombinant interleukin-2; Circles=50 kD membrane, genetically engineered glycoprotein (Mr>100 kD). All examples shown are from plasma protein-free continuous perfusion fermentation.

During the inventive method of using device A, the transmembrane pressure of the integrated continuous ultrafiltration is going to increase with time, while the specific membrane flux (in liters/hour/m$^2$/bar) is decreasing at constant volumetric throughput. This is common to all ultrafiltration processes and is due to effects like concentration polarization, gel-layer formation and fouling. However, in contrast to batch ultrafiltration, as can be seen from the example shown in FIG. 12, the changes of pressure and specific flux are extremely slow with device A, allowing continuous operation for weeks at a time, before the membranes need to be cleaned or replaced. Additionally, the rate of change and overall performance of the system is quite insensitive to the product produced or the cell-line used in the continuous perfusion fermentation (FIG. 12). Therefore, the inventive device A and respective method is also ideally suited as a generic platform for rapid production of various proteins since it performs robustly and predictably with various target proteins from different cell-lines.

Figure 13:
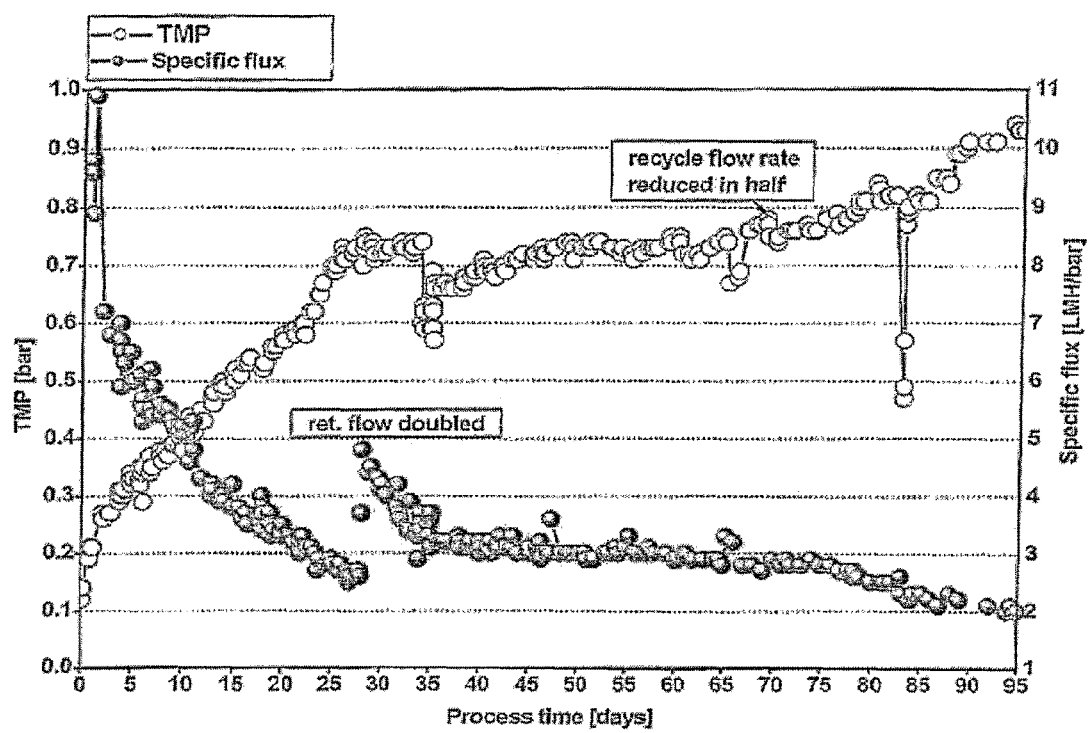
FIG. 13: Example of long-term performance of inventive device A directly coupled to continuous perfusion fermentation of cell-line co-expressing 2 protein products (Green fluorescent protein GFP and IL-2SA). Transmembrane pressure and specific flux of inventive continuous ultrafiltration system (300) as a function of continuous process time shown. 10 kD membrane was used.

Surprisingly, applicants discovered that the negative effects of gel-layer formation and fouling are in fact so much minimized with device A, that a much larger total volume per installed ultrafilter area can be processed, before cleaning or replacement of filters becomes necessary. FIG. 13 shows the robust performance of the inventive device A in a long-term run. After approximately 25 days, the transmembrane pressure surprisingly appeared to stabilize in a quasi-steady-state, suggesting even higher long-term performance. On day 27, the retentate flow rate was purposefully doubled to test the effect of higher throughput. After 34 days, a short flush was performed with sterile 0.5 M NaOH, without opening the system, and thus while maintaining full system integrity and sterility. After this, the TMP again stabilized, or at least increased only at an extremely low rate. After 70 days of continuous, sterile operation, the recycle flow rate was purposefully reduced in half to test the effect on system performance. As expected, the TMP started to increase with a somewhat higher rate due to the reduced mass transfer and thus increased wall concentration at the membrane surface. However, 95 days of operation were successfully and robustly completed before the system was turned off. A total of close to 4500 liters have been processed per m$^2$ of membrane area, with minimal manual labor (daily sampling only). In comparison, the optimized conventional batch ultrafiltration process for the same application has 45-fold less loading capacity, at approx. 100 l/m$^2$, and requires at least 1-2 operators full time.

Figure 14:
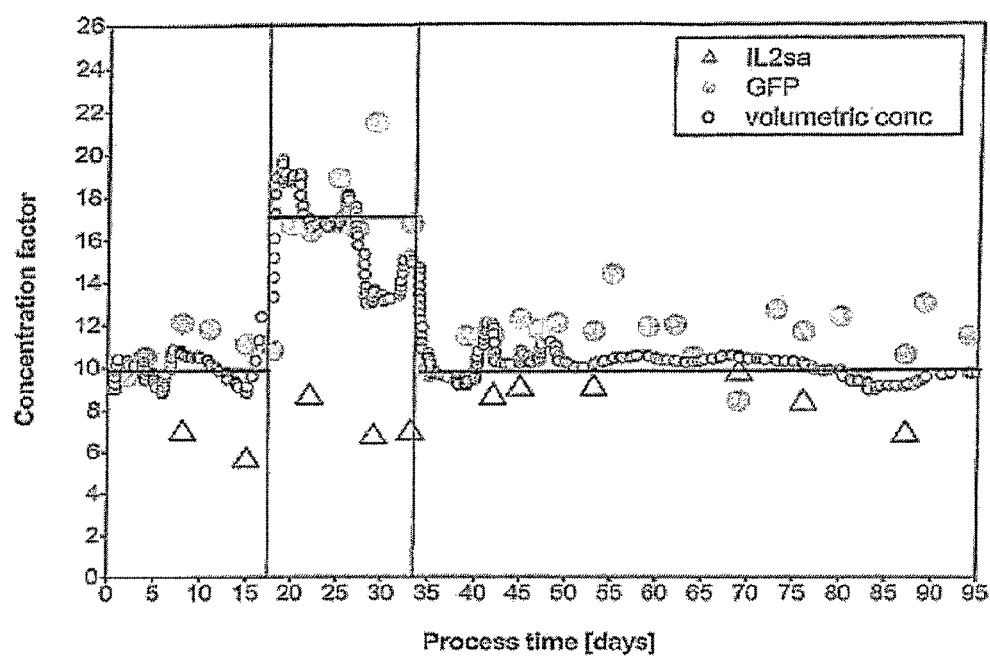
FIG. 14: Example of long-term performance of inventive device A directly coupled to continuous perfusion fermentation of cell-line co-expressing 2 protein products (Green fluorescent protein GFP and IL-2SA). 10 kD membrane was used. Concentration factor of both protein products, as determined by specific assays, and volumetric concentration factor shown as a function of continuous process time.

Also surprisingly, the selectivity of the inventive device A, in particular its integrated continuous ultrafiltration system (300), proved to be significantly higher then the selectivity of a conventional batch process. It is well known to those familiar with the field that in conventional batch ultrafiltration, a secondary membrane is formed from retained macromolecules during the initial stage of the process (gel layer), which reduces the apparent molecular weight cut-off. The result is that both the target molecule and contaminating smaller proteins are retained, which makes significant simultaneous purification practically impossible. Therefore, with conventional batch ultrafiltration it is seldom possible to separate proteins that are less then a factor of 10 apart in terms of their molecular weight. However, as can be seen from FIG. 14, with the inventive integrated continuous ultrafiltration process it is possible to adjust conditions to efficiently separate IL-2SA (approx. 16 kD) and green fluorescent protein GFP (27-30 kD). This higher then expected separation performance does allow for simultaneous concentration and purification.

Benefits of Device B and Respective Method

Figure 15:
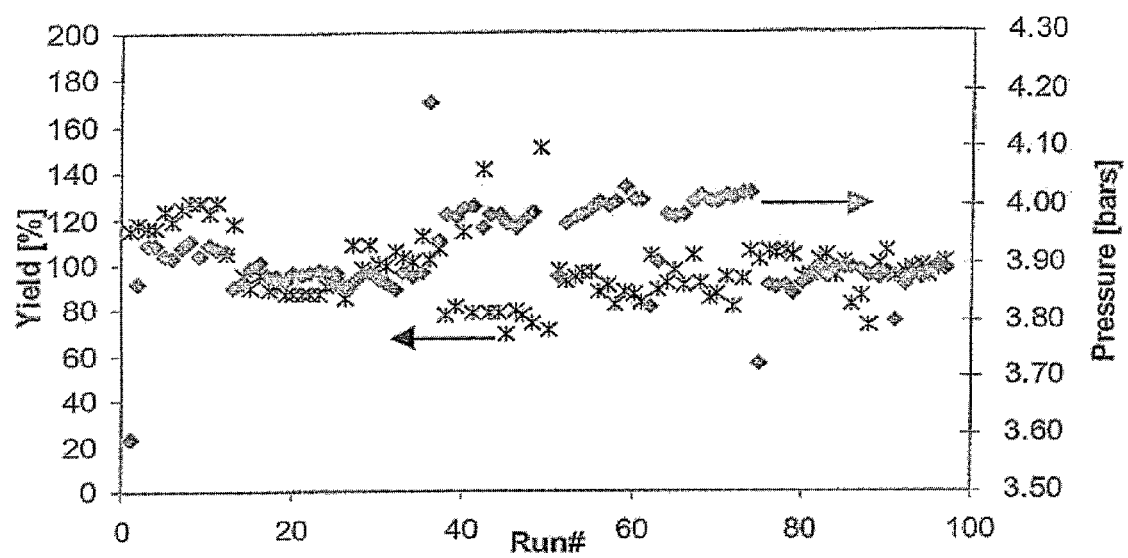
FIG. 15: Example for performance of inventive device B. Yield and pressure drop over close to 100 consecutive adsorption/desorption cycles with convective adsorber (target protein: genetically engineered blood coagulation Factor FVIII variant; convective adsorber: commercial adsorber, Mustang Q, Pall Corporation).

FIG. 15 illustrates the performance of the inventive device B. Using a commercial convective adsorber (Mustang Q, Pall Corporation, 15 layer module), close to 100 consecutive adsorption/desorption cycles have been performed, thereby concentrating and purifying a recombinant FVIII variant from continuous perfusion culture. The average yield achieved was approximately 95% (spread results from assay variation), while the pressure remained relatively constant over the entire number of cycles performed. Therefore, it can be specified that at least 100 consecutive cycles can be performed before exchanging the adsorber set-up.

As has been shown in the detail description of the method of using inventive device B, the total mean residence time of the product in a present embodiment is less than 3 hours, before it is eluted in concentrated, purified and stabilized form in an appropriate buffer. This is significantly less then the more than 24 hours residence time in a conventional batch isolation process performed once daily and therefore results in significantly higher yields of the inherently labile protein products. In a present embodiment described before, approximately 13 cycles are performed per day, which means in context of FIG. 15 that the semi-continuous adsorber assembly would need to be exchanged only every 7-8 days, which is done without compromising sterility and continuity of operation.

Figure 16:
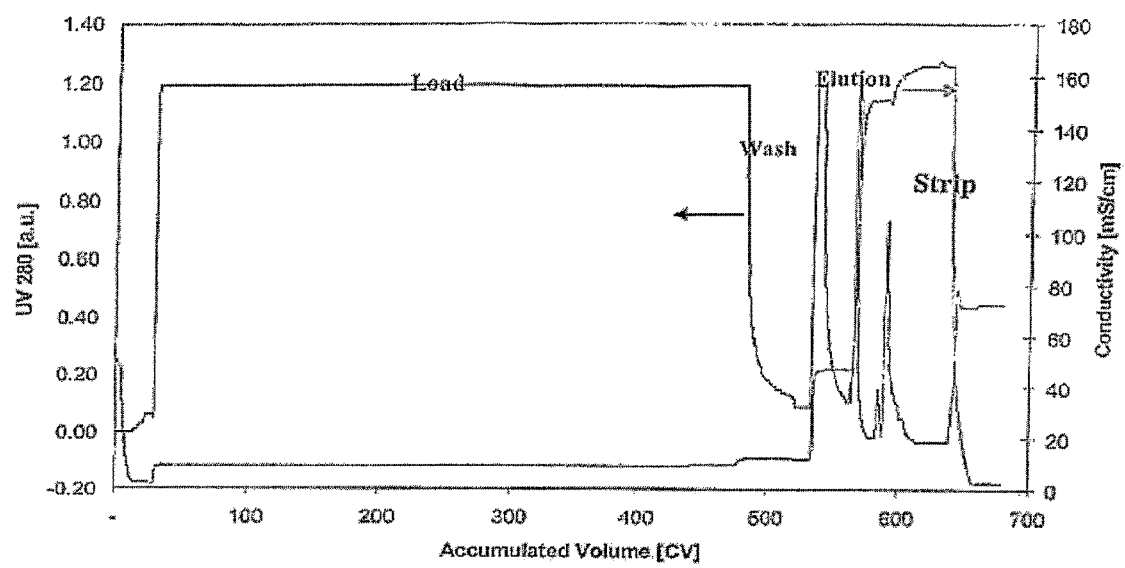
FIG. 16: Example for performance of inventive device B. UV and conductivity profile during a typical adsorption/desorption cycle with convective adsorber (target protein: genetically engineered blood coagulation Factor FVIII variant; convective adsorber: commercial adsorber, Mustang Q, Pall Corporation).

FIG. 16 shows an example of the UV and conductivity profile over a single typical adsorption/desorption and regeneration cycle with device B. It can be seen that more then 450 adsorber volumes (CVs) can be loaded, while the product elutes in a very sharp peak. Contaminants are removed significantly in the flow through during the loading phase, as well as, during the wash and the strip (regeneration phase).

Figure 17:
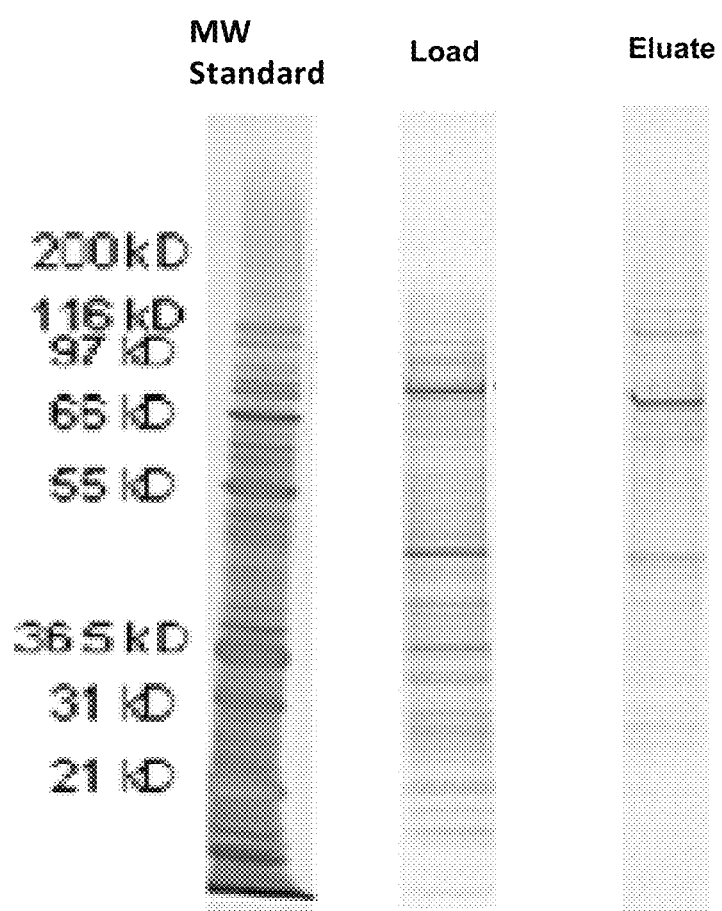
FIG. 17: Example for performance of inventive device B. SDS-Page gel (silver stained) of Load=clarified harvest continuously leaving the particle removal system (100) and semi-continuously loaded onto the convective adsorber system (400) and typical adsorption/desorption eluate shown. Target protein: genetically engineered blood coagulation Factor FVIII variant; convective adsorber: commercial adsorber, Mustang Q, Pall Corporation). Eluate was diluted back to load concentration before run on gel.

FIG. 17 illustrates the purification performance of the inventive process comprising semi-continuous convective adsorption/desorption. An example SDS page gel of a FVIII variant isolate is shown. As can be seen, the eluate fractions, which include 95% of the loaded FVIII variant (as determined by separate activity assay), contain significantly less protein than the load and are thus purified. No additional degradation bands are visible in the eluate (isolate), indicating excellent product quality.

In summary, the inventive device B is able to achieve similar purification performance as comparable batch processes, while at the same time minimizing yield losses for inherently unstable protein products, as well as, product quality issues, due to the minimization of product residence time. At the same time, labor costs are dramatically reduced due to the inherently high degree of automation of the inventive process, requiring minimal operator intervention.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Accordingly, it is to be understood that the embodiments of the invention herein providing for an improved method of filtration to generate a high yield of a molecule of interest from a given feedstream are merely illustrative of the application of the principles of the invention. It will be evident from the foregoing description that changes in the form, methods of use, and applications of the elements of the disclosed may be resorted to without departing from the spirit of the invention, or the scope of the appended claims.

We claim:

1. A process for partially purifying and concentrating a labile protein of interest from a heterogeneous tissue culture fluid mixture, consisting of the steps:
    (a) producing by a continuous perfusion fermentation process a heterogeneous tissue culture fluid mixture containing a labile protein of interest;
    (b) transferring the tissue culture fluid mixture to a continuous particle removal process integrated with the continuous perfusion fermentation system;
    (c) removing particulate contaminants from the tissue culture fluid in the continuous particle removal process to produce a clarified tissue culture fluid containing the protein of interest;
    (d) transferring the clarified tissue culture fluid to one or more surge vessels integrated with the continuous particle removal process;
    (e) optionally adjusting the pH, ionic strength, or protein stabilization properties of the clarified tissue culture fluid; and
    (f) transferring the clarified tissue culture fluid to one or more convective ion exchange adsorber/desorber membranes integrated with the surge vessels; and
    (g) purifying the protein of interest from the clarified tissue culture fluid in the convective ion exchange adsorber/desorber membranes to produce a particle-free, concentrated and partially purified protein of interest; wherein a specific flow rate of the mixture through the continuous perfusion fermentation process and continuous particle removal process is maintained substantially constant and wherein a loading flow rate through the convective ion exchange adsorber/desorber membrane is greater than the specific flow rate.

2. The process according to claim 1, wherein the protein of interest is Factor VIII.

3. A process for partially purifying and concentrating a labile protein of interest from a heterogeneous tissue culture fluid mixture, consisting of the steps:
    (a) producing by a continuous perfusion fermentation process a heterogeneous tissue culture fluid mixture containing a labile protein of interest;
    (b) transferring the tissue culture fluid mixture to a continuous particle removal process integrated with the continuous perfusion fermentation system;
    (c) removing particulate contaminants from the tissue culture fluid in the continuous particle removal process to produce a clarified tissue culture fluid containing the protein of interest;
    (d) transferring the clarified tissue culture fluid to one or more surge vessels integrated with the continuous particle removal process;
    (e) adjusting the pH, ionic strength, or protein stabilization properties of the clarified tissue culture fluid; and
    (f) transferring the clarified tissue culture fluid to one or more convective ion exchange adsorber/desorber membranes integrated with the surge vessels; and
    (g) purifying the protein of interest from the clarified tissue culture fluid in the convective ion exchange adsorber/desorber membranes to produce a particle-free, concentrated and partially purified protein of interest; wherein a specific flow rate of the mixture through the continuous perfusion fermentation process and continuous particle removal process is maintained substantially constant and wherein a loading flow rate through the convective ion exchange adsorber/desorber membrane is greater than the specific flow rate.

4. The process according to claim 3, wherein the labile protein of interest is Factor VIII.

\* \* \* \* \*